(12) United States Patent
Bürli et al.

(10) Patent No.: US 8,765,762 B2
(45) Date of Patent: *Jul. 1, 2014

(54) PYRAZOLOPYRIDAZINES AND METHODS FOR TREATING RETINAL-DEGERATIVE DISEASES AND HEARING LOSS ASSOCIATED WITH USHER SYNDROME

(71) Applicant: Usher III Initiative, Chicago, IL (US)

(72) Inventors: Roland Werner Bürli, Bishop's Stortford (GB); William Rameshchandra Krishna Esmieu, Cambridge (GB); Christopher James Lock, Burwell (GB); Karine Fabienne Malagu, Saffron Walden (GB); Andrew Pate Owens, Huntingdon (GB); William E. Harte, Moorpark, CA (US)

(73) Assignee: Usher III, Initiative, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/791,675

(22) Filed: Mar. 8, 2013

(65) Prior Publication Data

US 2014/0121205 A1      May 1, 2014

Related U.S. Application Data

(60) Provisional application No. 61/718,593, filed on Oct. 25, 2012.

(51) Int. Cl.
*A61K 31/497* (2006.01)
*C07D 231/12* (2006.01)

(52) U.S. Cl.
USPC ..................... 514/252.05; 544/241

(58) Field of Classification Search
USPC .............. 514/252.05; 544/238, 241
See application file for complete search history.

(56) References Cited

U.S. PATENT DOCUMENTS

| | | | |
|---|---|---|---|
| 7,390,808 B2 | 6/2008 | Green et al. | |
| 7,666,647 B2 | 2/2010 | ter Haar et al. | |
| 7,812,166 B2 | 10/2010 | Dai et al. | |
| 7,883,881 B2 | 2/2011 | ter Haar et al. | |
| 8,318,467 B2 | 11/2012 | ter Haar et al. | |
| 8,338,439 B2 | 12/2012 | Singh et al. | |
| 8,450,335 B2 | 5/2013 | Singh et al. | |
| 2008/0194562 A1 | 8/2008 | Wyatt et al. | |
| 2010/0029610 A1 | 2/2010 | Singh et al. | |
| 2013/0065879 A1 | 3/2013 | Singh et al. | |
| 2013/0065899 A1 | 3/2013 | Singh et al. | |
| 2013/0072469 A1 | 3/2013 | Singh et al. | |
| 2013/0165462 A1 | 6/2013 | Singh et al. | |
| 2013/0252936 A1 | 9/2013 | Bürli et al. | |

FOREIGN PATENT DOCUMENTS

| | | |
|---|---|---|
| WO | WO 03/080616 | 10/2003 |
| WO | WO 2012/148994 | 11/2012 |

OTHER PUBLICATIONS

International Search Report and Written Opinion for International Application No. PCT/US2012/034959, mailed Sep. 21, 2012, 10 pages.
El-Amraoui, A. et al., "Usher I Syndrome: unravelling the mechanisms that underlie the cohesion of the growing hair bundle in inner ear sensory cells," Journal of Cell Science, 118(20):4593-4603 (2005).
Tian, G. et al., "Clarin-1, encoded by the Usher Syndrome III causative gene, forms a membranous microdomain," The Journal of Biological Chemistry, 284(28):18980-18993 (2009).
U.S. Appl. No. 13/791,744, filed Mar. 8, 2013, entitled "Pyrazolopyridazines and Methods for Treating Rental-Degerative Diseases and Hearing Loss Associated With Usher Syndrome".
International Search Report and Written Opinion for International Application No. PCT/US2013/066938, mailed Jan. 30, 2014.
International Search Report and Written Opinion for International Application No. PCT/US2013/066939, mailed Mar. 5, 2014.
Brana, M. F. et al., "Pyrazolo[3,4-c]pyridazines as Novel and Selective Inhibitors of Cyclin-Dependent Kinases," J. Med. Chem., 48(22):6843-6854 (2005).
Churcher, I., "Tau Therapeutic Strategies for the Treatment of Alzheimer's Disease," Current Topics in Medicinal Chemistry, 6(6):579-595 (2006).
Tretyakov, E. V. et al., "Investigations of the Richter reaction in a series of vicinal alkynylpyrazolediazonium salts," J. Chem. Soc., Perkin Trans., 1(24):3721-3726 (1999).

*Primary Examiner* — Raymond Henley, III
(74) *Attorney, Agent, or Firm* — Cooley LLP

(57) ABSTRACT

Compounds, compositions and methods for the treatment of retinal degenerative diseases, such as retinitis pigmentosa, Leber's congenital Amaurosis, Syndromic retinal degenerations, age-related macular degeneration and Usher Syndrome, and hearing loss associated with Usher Syndrome are described herein.

18 Claims, 1 Drawing Sheet

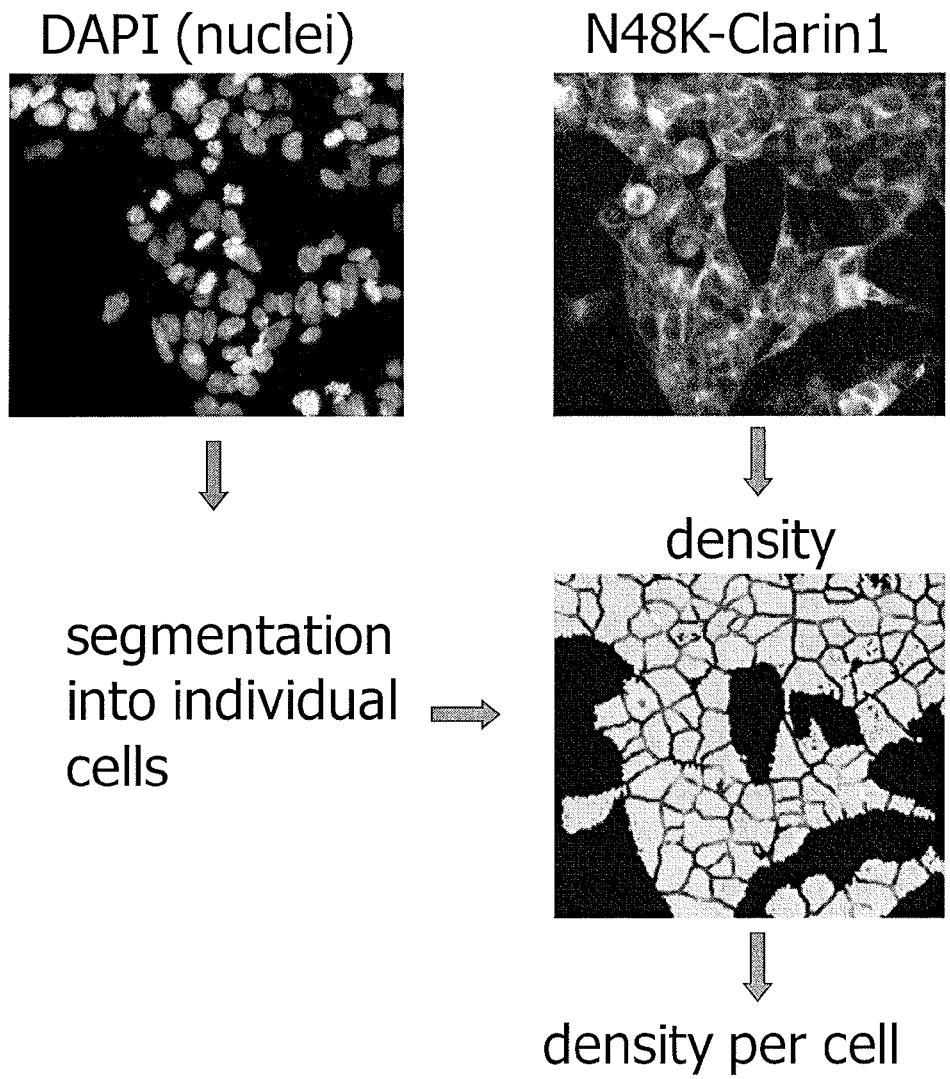
High content analysis. DAPI-stained nuclei are used to perform segmentation of the image into individual cells. The density observed in the N48K Clarin-1 channel (Cy3) is then calculated per cell and averaged over a field.

PYRAZOLOPYRIDAZINES AND METHODS FOR TREATING RETINAL-DEGERATIVE DISEASES AND HEARING LOSS ASSOCIATED WITH USHER SYNDROME

This application claims the benefit of U.S. Provisional Application No. 61/718,593, filed Oct. 25, 2012, the disclosure of which is hereby incorporated by reference herein in its entirety.

BACKGROUND OF THE INVENTION

Usher Syndrome, a rare genetic disorder and a leading cause of deafness and blindness, is associated with a mutation in any one of ten genes. Other names for the syndrome include Hallgren Syndrome, Usher-Hallgren Syndrome, RP-Dysacusis Syndrome, and Dystrophia Retinae Dysacusis Syndrome.

Usher Syndrome is characterized by deafness and gradual vision loss. The hearing loss is associated with inner ear defects, whereas the vision loss is associated with retinitis pigmentosa (RP), a degeneration of the retinal cells. Usually, the rod cells of the retina are affected first, leading to early night blindness and the gradual loss of peripheral vision. Some cases involve early degeneration of the cone cells of the macula, leading to a loss of central acuity. In some cases, the sufferer's foveal vision is spared, leading to "doughnut vision," in which central and peripheral vision remain intact, but interrupted by a ring of blindness.

Usher Syndrome has three clinical subtypes, denoted: I, II and III. Usher I subjects are born profoundly deaf, begin to lose vision within ten years and exhibit balance difficulties. They are slow to learn to walk as children, due to vestibular abnormalities. Usher II subjects suffer lesser hearing loss, do not suffer physical imbalance and begin to lose vision in adolescence. Much of their hearing can be preserved into middle age. Usher III subjects suffer gradual loss of hearing and vision and can suffer physical imbalance.

Usher Syndrome is a variable condition; the degree of severity is not tightly linked to subtype. For example, an Usher III subject might be asymptomatic in childhood, but develop profound hearing and vision loss by early to mid adulthood. Substantial visual impairment prior to age 50 is common in Usher III subjects. An Usher I subject, on the other hand, might be deaf from birth, but sustain good central vision into old age.

SUMMARY OF THE INVENTION

The invention provides compounds having the following structures:

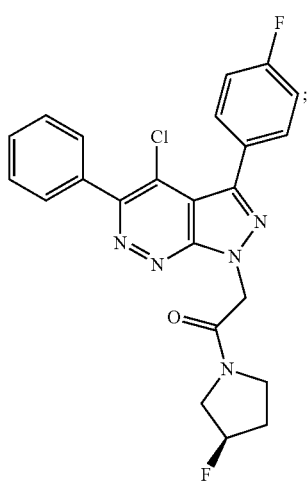

1

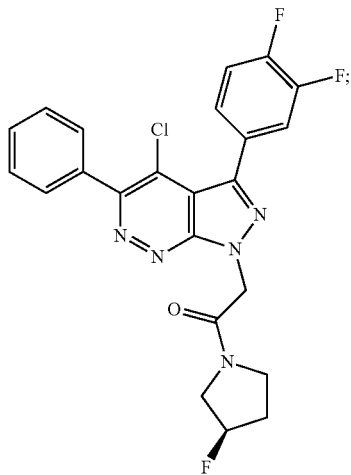

2

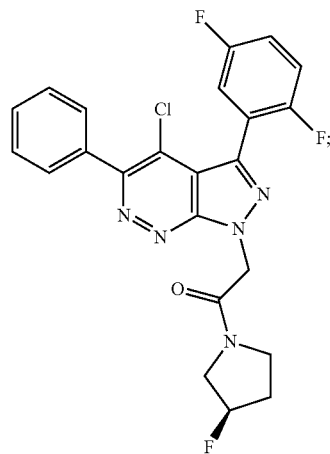

3

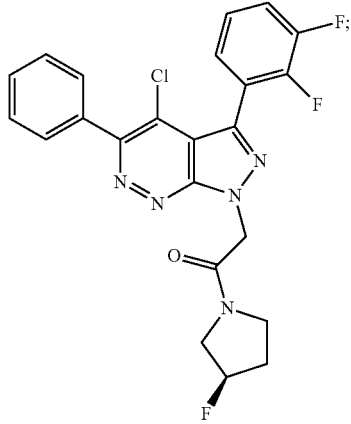

4

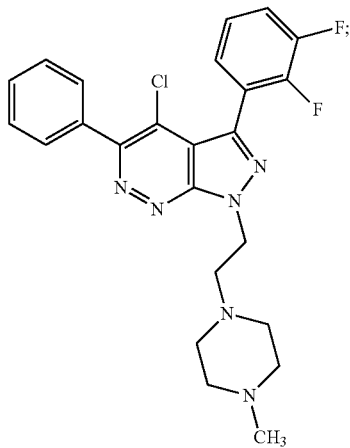
5
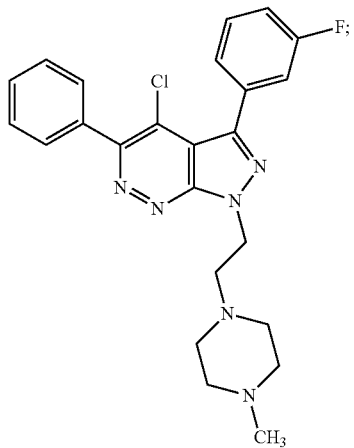
8
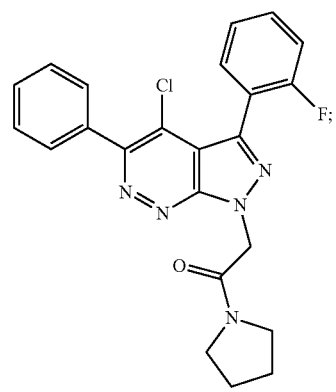
6
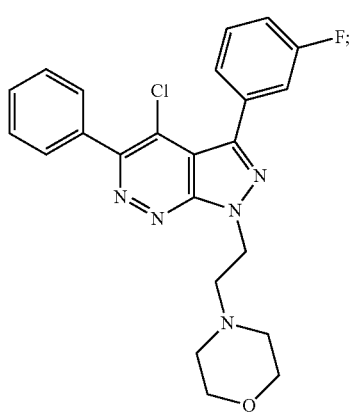
9
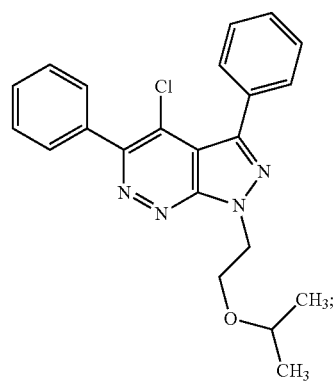
7
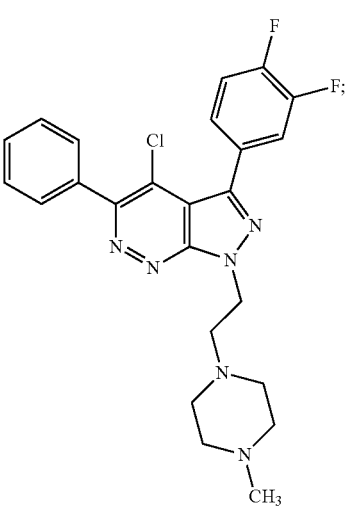
10

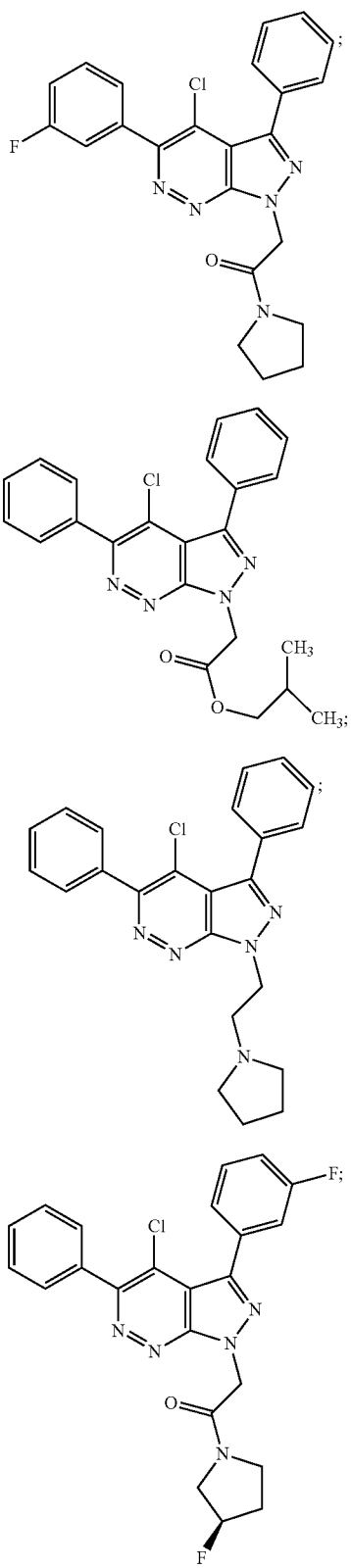

and pharmaceutically acceptable salts thereof.

Each of the above Compounds 1-14, or a pharmaceutically acceptable salt thereof, (a "Pyrazolopyridazine compound" or a "compound of the invention") is useful for treating a retinal degenerative disease or hearing loss associated with Usher Syndrome.

The invention further provides compositions comprising an effective amount of a Pyrazolopyridazine compound and a pharmaceutically acceptable carrier or vehicle. The compositions are useful for treating a retinal degenerative disease or hearing loss associated with Usher Syndrome.

The invention further provides methods for treating a retinal degenerative disease, comprising administering to a subject in need thereof an effective amount of a Pyrazolopyridazine compound.

The invention still further provides methods for treating hearing loss associated with Usher Syndrome, comprising administering to a subject in need thereof an effective amount of a Pyrazolopyridazine compound.

BRIEF DESCRIPTION OF THE FIGURE

FIG. 1 illustrates density of N48K Clarin-1 expression in cells.

DETAILED DESCRIPTION OF THE INVENTION

The invention provides compounds of the invention, compositions comprising a compound of the invention, and methods for treating a retinal degenerative disease or hearing loss associated with Usher Syndrome, comprising administering a Pyrazolopyridazine compound or a pharmaceutically acceptable salt thereof.

Compounds of the Invention

The word "about" when immediately preceding a numerical value means a range of plus or minus 10% of that value, e.g., "about 100 mg" means 90 mg to 110 mg, "about 300 mg" means 270 mg to 330 mg, etc.

Abbreviations

APCI Atmospheric Pressure Chemical Ionization
DAPI 4',6-diamidino-2-phenylindole
DIPEA diisopropylethylamine
DMEM Dulbecco's Modified Eagle Medium
DMF dimethylformamide
DMSO Dimethyl sulfoxide
EDAC 1-(3-dimethylaminopropyl)-3-ethylcarbodiimide hydrochloride
ESI Electrospray ionization
ESI-TOF Electrospray ionization-Time-of-flight
HATU 2-(7-Aza-1H-benzotriazole-1-yl)-1,1,3,3-tetramethyluronium hexafluorophosphate
HOPO 2-hydroxypyridine-N-oxide
HPLC High-performance liquid chromatography
LCMS Liquid chromatography-mass spectrometry
LDA lithium diisopropyl amide
m/z Mass-to-charge ratio
MALDI-TOF Matrix Assisted Laser Desorption Ionization-Time-of-flight
MS Mass spectrometry
PBS phosphate-buffered saline
Rt Retention time
SDS sodium dodecylsulfate
THF tetrahydrofuran The invention provides compounds having the following structures:

1
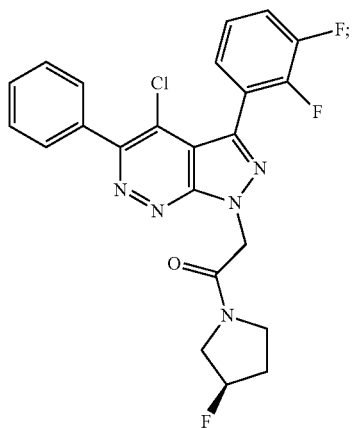
2
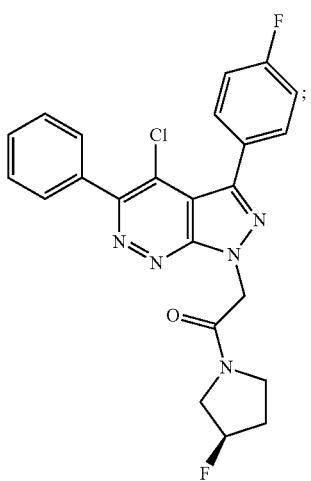
3
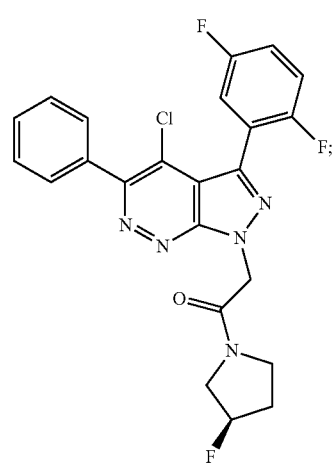
4
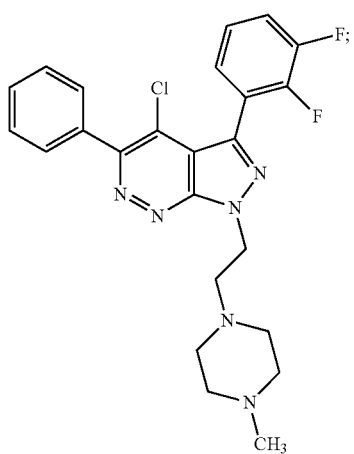
5
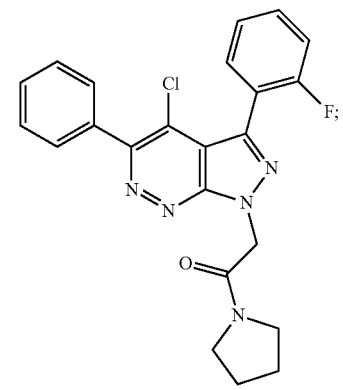
6
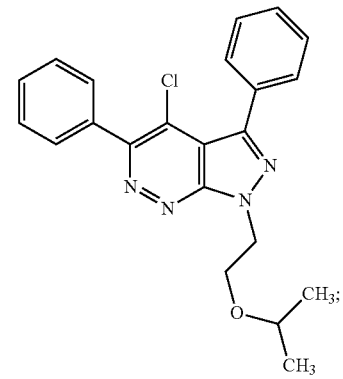
7

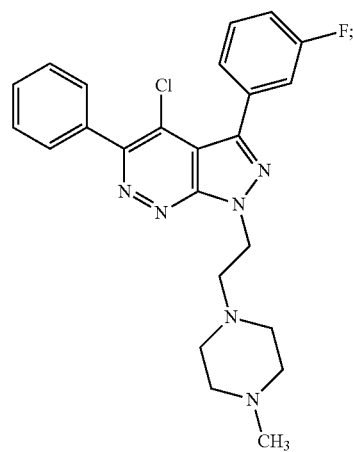
8
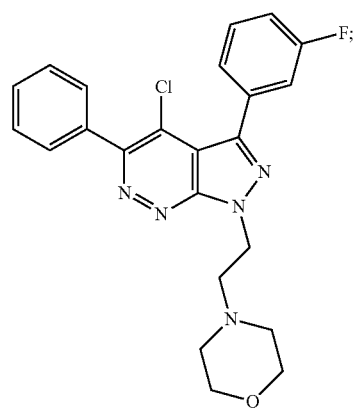
9
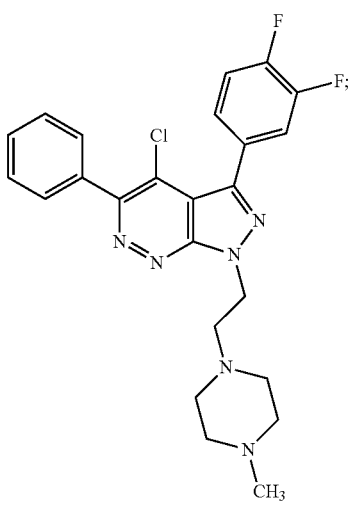
10
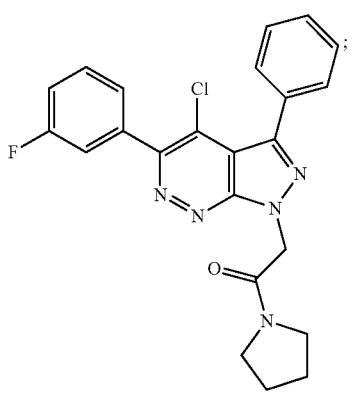
11
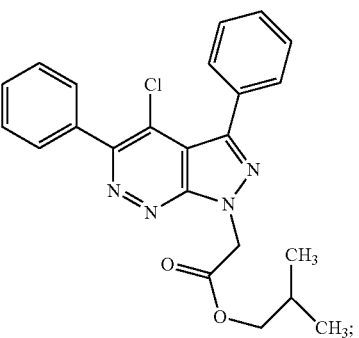
12
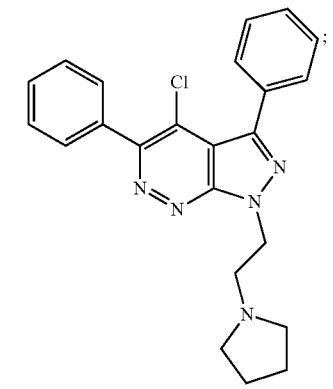
13
14
and pharmaceutically acceptable salts thereof.
Some of the compounds disclosed herein, for example, Compounds 1-4 and 14, are depicted having a bold or hatched wedge, indicating absolute stereochemistry.

Without being bound by any particular mechanism, it is believed that the bisphenyl pyrazolopyridazine moiety of Pyrazolopyridazine compounds is involved in the restoration of the activity and trafficking of Clarin I, which is the protein encoded by the gene mutated in Usher III Syndrome (Adato et al., Eur J Hum Genet. 2002 June; 10(6):339-50)

The compounds of the invention can be in the form of a salt. In some embodiments, the salt is a pharmaceutically acceptable salt. Pharmaceutically acceptable salts include, for example, acid-addition salts and base-addition salts. The acid that forms an acid-addition salt can be an organic acid or an inorganic acid. A base that forms a base-addition salt can be an organic base or an inorganic base. In some embodiments, a pharmaceutically acceptable salt is a metal salt. In some embodiments, a pharmaceutically acceptable salt is an ammonium salt.

Acid-addition salts can arise from the addition of an acid to the free-base form of a compound of the invention. In some embodiments, the acid is organic. In some embodiments, the acid is inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid-addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methyl maleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound of the invention having a carboxyl group. The inorganic base consists of a metal cation paired with a basic couterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, cesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a cesium salt, a cerium salt, a magnesium salt, a manganese salt, an iron salt, a calcium salt, a strontium salt, a cobalt salt, a titanium salt, a aluminum salt, a copper salt, a cadmium salt, and a zinc salt.

Ammonium salts can arise from the addition of ammonia or an organic amine to a compound of the invention having a carboxyl group. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts include is a triethylammonium salt, a diisopropylammonium salt, an ethanolammonium salt, a diethanolammonium salt, a triethanolammonium salt, a morpholinium salt, an N-methylmorpholinium salt, a piperidinium salt, an N-methylpiperidinium salt, an N-ethylpiperidinium salt, a dibenzylammonium salt, a piperazinium salt, a pyridinium salt, a pyrrazolium salt, an imidazolium salt, a pyrazinium salt, an ethylenediammonium salt, an N,N'-dibenzylethylenediammonium salt, a procaine salt, a chloroprocaine salt, a choline salt, a dicyclohexylammonium salt, and a N-methylglucamine salt.

Methods for Making the Pyrazolopyridazine Compounds

Pyrazolopyridazine compounds include the following.

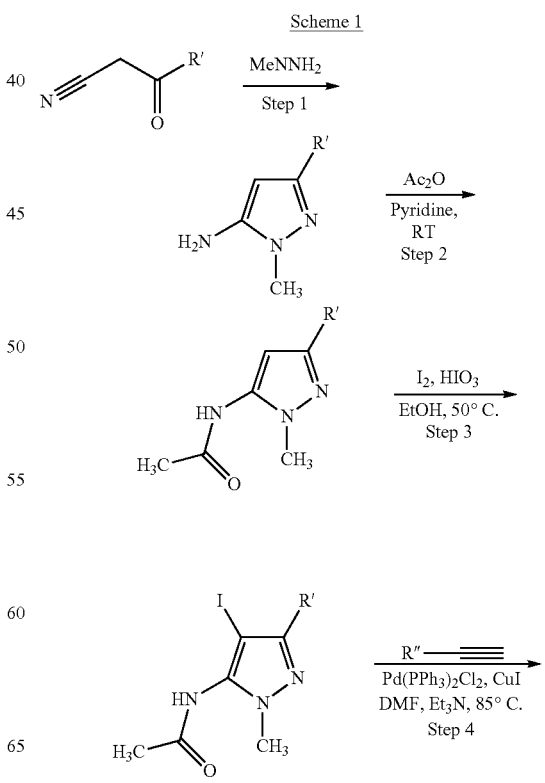

-continued

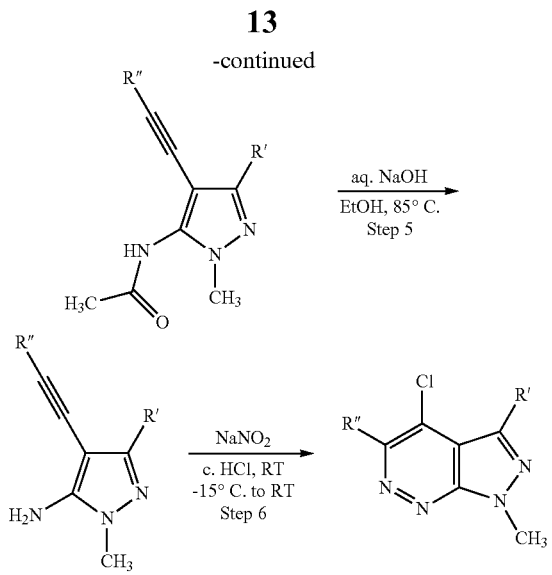

Scheme 1 generally describes the preparation of Pyrazolopyridazine compounds having a 1-N-methyl group and where R' and R" are independently an unsubstituted or a substituted phenyl group. For example, a 2-cyanocarbonyl compound in which R' is unsubstituted or substituted phenyl is condensed with N-methylhydrazine to provide a 3-substituted-1-methyl-1H-pyrazol-5-amine. The 5-amino group is acylated, for example, with acetic anhydride in the presence of a base, such as pyridine, to provide a 5-amido compound. The 5-amido compound is iodinated, for example, with a mixture of iodine and iodic acid in a solvent such as ethanol (EtOH) to provide an N-(3-substituted-4-iodo-1-methyl-1H-pyrazol-5-yl)acetamide. A palladium-mediated cross-coupling, such as a Sonagashira cross-coupling, of the acetamide with an R"-substituted terminal alkyne, catalyzed, for example, by a palladium complex such as palladium (II) bistriphenylphosphine dichloride in the presence of copper (I) iodide in a solvent such as dimethylformamide (DMF) with a base such as triethylamine provides a disubstituted alkyne in which R" is unsubstituted or substituted phenyl. Saponification of the alkyne acetamide with a base such as sodium hydroxide in a solvent such as ethanol provides the primary amine. Diazotization of the primary amine with sodium nitrite in concentrated hydrochloric acid provides a diazo intermediate, which cyclizes to provide a Pyrazolopyridazine compound having a 1-N-methyl group and where R' and R" are independently an unsubstituted or a substituted phenyl group.

Scheme 2

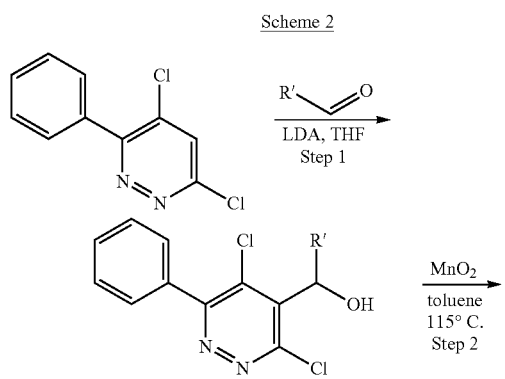

-continued

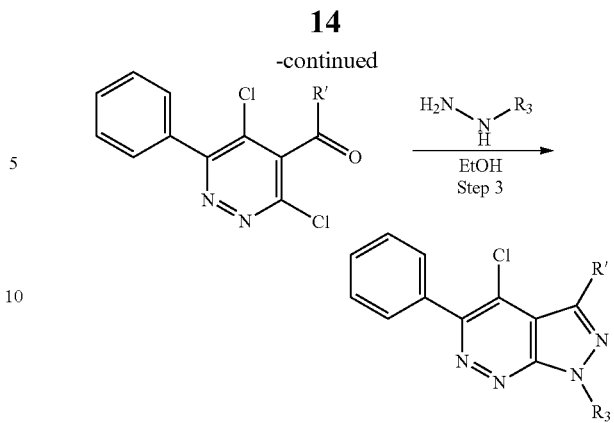

Scheme 2 generally describes the preparation of Pyrazolopyridazine compounds having an $R_3$ group and in which R' is an unsubstituted or a substituted phenyl group. R' and $R_3$ can be the same or different. For example, 4,6-dichloro-3-phenylpyridazine is deprotonated with a base such as lithium diisopropyl amide (LDA) in a solvent such as tetrahydrofuran (THF), and the resultant 5-lithio species is condensed with an unsubstituted or a substituted benzaldehyde to provide a secondary alcohol. The alcohol is oxidized to a ketone with an oxidizing agent such as manganese dioxide in a solvent such as toluene. The ketone is condensed with an $R_3$-substituted hydrazine in a solvent such as ethanol to provide an intermediate hydrazone, which cyclizes to provide a Pyrazolopyridazine compound having a 1-N—$R_3$ group, in which $R_3$ is defined as in Formulas II and III and in which R' is an unsubstituted or a substituted phenyl group.

Scheme 3

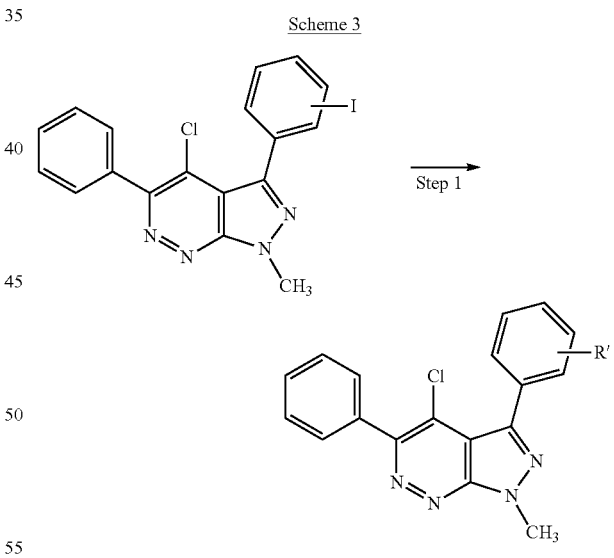

Scheme 3 generally describes the preparation of Pyrazolopyridazine compounds having a 1-N-methyl group and where R' is a cyano group, an alkyne, an alkene or an aryl group. For example, 1-methyl-3-iodophenyl-4-chloro-5-phenyl-1H-pyrazolo[3,4-c]pyridazine is coupled with a suitable coupling partner, such as a cyanide salt, a terminal alkyne, an alkenyl halide, or an aryl halide, optionally in the presence of a suitable catalyst such as a palladium complex, optionally in the presence of a non-palladium transition metal salt such as a zinc or copper salt, optionally in the presence of an additive such as triphenylphosphine or an organic amine base, to provide a Pyrazolopyridazine compound having a 1-N-methyl group and where R' is a cyano group, an alkyne, an alkene or an aryl group. The position of R', i.e., ortho, meta or para, in the product is the same as the position of the iodo group in the starting material.

Scheme 4

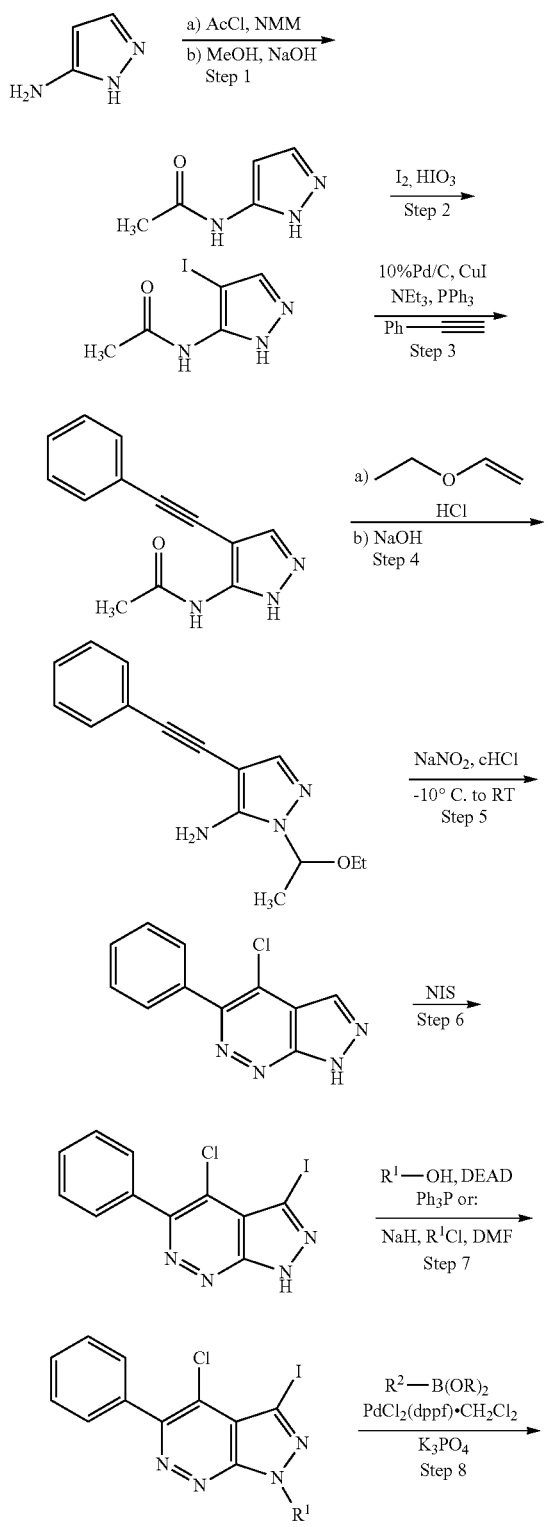

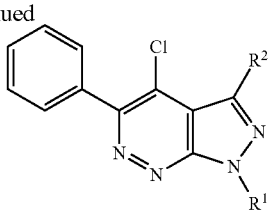

Scheme 4 generally describes the preparation of Pyrazolopyridazine compounds.

Therapeutic Uses

A compound of the invention can be administered to a subject in need thereof for the treatment of a retinal degenerative disease. Non-limiting examples of retinal degenerative diseases include: retinitis pigmentosa, Leber's congenital Amaurosis, Syndromic retinal degenerations, age-related macular degeneration including wet and dry age-related macular degeneration, and Usher Syndrome. In some embodiments, the Usher Syndrome is a subtype of Usher Syndrome. In some embodiments, the subtype is Usher I. In some embodiments, the subtype is Usher II. In some embodiments, the subtype is Usher III.

In a further embodiment of the invention, a compound of the invention can be administered to a subject in need thereof for the treatment of hearing loss associated with Usher Syndrome. In some embodiments, the Usher Syndrome is a subtype of Usher Syndrome. In some embodiments, the subtype is Usher I. In some embodiments, the subtype is Usher II. In some embodiments, the subtype is Usher III.

A "subject" is a mammal, e.g., a human, mouse, rat, guinea pig, dog, cat, horse, cow, pig, or non-human primate, such as a monkey, chimpanzee, baboon or rhesus. In one embodiment, the subject is a human.

The compounds of the invention can be administered to a subject as a component of a composition that comprises a pharmaceutically acceptable carrier or vehicle. Non-limiting examples of suitable pharmaceutical carriers or vehicles include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol, buffered water, and phosphate buffered saline. These compositions can be administered as, for example, drops, solutions, suspensions, tablets, pills, capsules, powders, and sustained-release formulations. In some embodiments, the compositions comprise, for example, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate, and mineral oil. The compositions can additionally comprise lubricating agents, wetting agents, emulsifying and suspending agents, preserving agents, sweetening agents or flavoring agents.

The compositions can comprise an effective amount of a compound of the invention. An "effective amount" of a compound of the invention is an amount that is effective to treat a retinal degenerative disease or hearing loss associated with Usher Syndrome in a subject. The compositions can be formulated in a unit dosage form that comprises an effective amount of a compound of the invention. In some embodiments, the compositions comprise, for example, from about 1 ng to about 1,000 mg of a compound of the invention. In some embodiments, the compositions comprise from about 100 mg to about 1,000 mg of a compound of the invention. In some embodiments, the compositions comprise from about 100 mg to about 500 mg of a compound of the invention. In some embodiments, the compositions comprise from about 200 mg to about 300 mg of a compound of the invention.

The dosage of a compound of the invention can vary depending on the symptoms, age, and body weight of the subject, the nature and severity of the retinal degenerative disease or hearing loss associated with Usher Syndrome, the route of administration, and the form of the composition. The compositions described herein can be administered in a single dose or in divided doses. In some embodiments, the dosage of a compound of the invention ranges from about 0.01 ng to about 10 g per kg body mass of the subject, from about 1 ng to about 0.1 g per kg, or from about 100 ng to about 10 mg per kg.

Administration can be, for example, topical, intraaural, intraocular, parenteral, intravenous, intra-arterial, subcutaneous, intramuscular, intracranial, intraorbital, intraventricular, intracapsular, intraspinal, intracisternal, intraperitoneal, intranasal, aerosol, suppository, or oral. Formulations for oral use include tablets containing a compound of the invention in a mixture with non-toxic pharmaceutically acceptable excipients. These excipients can be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for ocular use can be in the form of eyedrops.

A compound of the invention or composition thereof can be provided in lyophilized form for reconstituting, for instance, in isotonic, aqueous, or saline buffers for parental, subcutaneous, intradermal, intramuscular, or intravenous administration. A composition of the invention can also be in the form of a liquid preparation useful for oral, intraaural, nasal, or sublingual administration, such as a suspension, syrup or elixir. A composition of the invention can also be in a form suitable for oral administration, such as a capsule, tablet, pill, and chewable solid formulation. A composition of the invention can also be prepared as a cream for dermal administration as a liquid, a viscous liquid, a paste, or a powder. A composition of the invention can also be prepared as a powder for pulmonary administration with or without an aerosolizing component.

The compositions can be in oral, intraaural, intranasal, sublingual, intraduodenal, subcutaneous, buccal, intracolonic, rectal, vaginal, mucosal, pulmonary, transdermal, intradermal, parenteral, intravenous, intramuscular and ocular dosage forms as well as being able to traverse the blood-brain barrier.

The compositions of the invention can be administered by various means known in the art. For example, the compositions of the invention can be administered orally, and can be formulated as tablets, capsules, granules, powders or syrups. Alternatively, compositions of the invention can be administered parenterally as injections (for example, intravenous, intramuscular or subcutaneous), drop infusion preparations or suppositories. For ophthalmic application compositions of the invention can be formulated as eye drops or eye ointments. Aural compositions can be formulated as ear drops, ointments, creams, liquids, gels, or salves for application to the ear, either internally or superficially. These formulations can be prepared by conventional means, and the compositions can be mixed with any conventional additive, such as an excipient, a binder, a disintegrating agent, a lubricant, a solubilizing agent, a suspension aid, an emulsifying agent, or a coating agent.

Compositions of the invention can include wetting agents, emulsifiers, and lubricants, coloring agents, release agents, coating agents, sweetening, flavoring and perfuming agents, preservatives and antioxidants.

Compositions can be suitable, for example, for oral, intraaural, intraocular, nasal, topical (including buccal and sublingual), rectal, vaginal, aerosol and/or parenteral administration. The compositions can be provided in a unit dosage form, and can be prepared by any methods known in the art.

Formulations suitable for oral administration may be in the form of capsules, cachets, pills, tablets, lozenges, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia. Compositions of the invention can also be administered as a bolus, electuary, or paste.

Additional examples of pharmaceutically acceptable carriers or vehicles include: (1) fillers or extenders, such as starches, lactose, sucrose, glucose, mannitol, and/or silicic acid; (2) binders, such as carboxymethyl cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as acetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; (10) coloring agents; and (11) buffering agents. Similar compositions can be employed as fillers in soft- or hard-filled gelatin capsules.

Liquid dosage forms for oral administration include pharmaceutically acceptable emulsions, microemulsions, gels, solutions, suspensions, syrups and elixirs. The liquid dosage form can contain inert diluents commonly used in the art, for example, water or other solvents, solubilizing agents and emulsifiers, such as ethyl alcohol, isopropyl alcohol, diethyl carbonate, ethyl acetate, benzyl alcohol, benzyl benzoate, propylene glycol, 1,3-butylene glycol, oils such as, cottonseed, groundnut, corn, germ, olive, castor and sesame oils, glycerol, tetrahydrofuryl alcohol, polyethylene glycols, fatty acid esters of sorbitan, and mixtures thereof.

Suspension dosage forms can contain suspending, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The dosage forms for transdermal administration of a subject composition include drops, powders, sprays, ointments, pastes, creams, lotions, gels, solutions, and patches. The ointments, pastes, creams, and gels can contain excipients, such as animal and vegetable fats, oils, waxes, paraffin, starch, tragacanth, cellulose derivatives, polyethylene glycols, silicones, bentonite, silicic acid, talc and zinc oxide, or mixtures thereof.

Powders and sprays can contain excipients such as lactose, talc, silicic acid, aluminum hydroxide, calcium silicates, polyamide powder, or mixtures thereof. Sprays may additionally contain customary propellants, such as chlorofluorohydrocarbons and volatile unsubstituted hydrocarbons, such as butane and propane.

Compositions can be administered by aerosol of solid particles. A non-aqueous (e.g., fluorocarbon propellant) suspension could be used. Sonic nebulizers can be used because they minimize exposure to shear, which might cause degradation.

An aqueous aerosol can be made by formulating an aqueous solution or suspension of a compound of the invention with any conventional pharmaceutically acceptable carriers or vehicles such non-ionic surfactants (Tweens, Pluronics, or polyethylene glycol); proteins such as serum albumin; sorbitan esters; fatty acids; lecithin; amino acids; buffers; salts; sugars; or sugar alcohols.

Compositions suitable for parenteral administration comprise a compound of the invention and one or more pharmaceutically acceptable sterile isotonic aqueous or non-aqueous solutions, dispersions, suspensions, or emulsions, or sterile powders which can be reconstituted into sterile injectable solutions or dispersions just prior to use, which can contain antioxidants, buffers, bacteriostats, or solutes, which render the formulation isotonic with the blood of the subject, and suspending or thickening agents.

Having described the invention with reference to certain embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

General Synthetic Methods

Unless otherwise stated, all chemicals were purchased from commercial suppliers and used without further purification.

Standard Basic LC-MS Conditions: (10 cm_ESCI_Bicarb_MeCN):

A Waters Xterra MS 5 μm C18, 100×4.6 mm (plus guard cartridge) using an acetonitrile (Far UV grade): water (high purity via PureLab Option unit) with 10 mM ammonium bicarbonate (ammonium hydrogen carbonate) gradient was used. The flow rate was 2 mL/min. UV detection was done using a Waters diode array detector (start Range 210 nm, end range 400 nm, range interval 4 nm). Mass detection was performed via a single quadrapole LC-MS instrument. Ionisation is either ESI or APCI dependent on compound types. The gradient used ran from 95% of aqueous solvent at time 0.00 min to 5% of aqueous solvent at 4.0 min. This percentage was then held for a further 1.5 min.

Standard Acidic HPLC Conditions. (10 cm_Formic_ACE 3 C18 AR_HPLC_CH$_3$CN)

A Hichrom ACE 3 C18-AR mixed mode 100×4.6 mm column using an acetonitrile (Far UV grade) with 0.1% (V/V) formic acid:water (high purity via PureLab Option unit) with 0.1% formic acid gradient was used. The flow rate was 1 mL/min. UV detection was done using an Agilent diode array detector (300 nm, band width 200 nm; ref. 450 nm, band width 100 nm). The gradient used ran from 98% of aqueous solvent from time 0.00 min to 3.00 min, to 100% of aqueous solvent at 12.00 min. This percentage was then held for a further 2.4 min.

Standard Basic HPLC Conditions: (15 cm_Bicarb_GeminiNX_HPLC)

A Phenomenex, Gemini NX, 3 μm C18, 150×4.6 mm column using an acetonitrile (Far UV grade): water (high purity via PureLab Option unit) with 10 mM ammonium bicarbonate gradient was used. The flow rate was 1 mL/min. UV detection was done using an Agilent diode array detector (300 nm, band width 200 nm; ref. 450 nm, band width 100 nm). The gradient used ran from 95.5% of aqueous solvent at time 0.00 min to 0% of aqueous solvent at 9.00 min. This percentage was then held for a further 4.5 min.

Standard Acidic HPLC Conditions: (15 cm_Formic_ASCENTIS_HPLC)

A Supelco, Ascentis® Express C18 or Hichrom Halo C18, 2.7 μm C18, 150×4.6 mm column using an acetonitrile (Far UV grade) with 0.1% (V/V) formic acid:water (high purity via PureLab Option unit) with 0.1% formic acid gradient was used. The flow rate was 1 mL/min. UV detection was done using an Agilent diode array detector (300 nm, band width 200 nm; ref. 450 nm, band width 100 nm). The gradient used ran from 96% of aqueous solvent at time 0.00 min to 0% of aqueous solvent at 9.00 min. This percentage was then held for a further 4.5 min.

Synthetic Preparation of Illustrative Compounds of the Invention

Example 1

2-[4-chloro-3-(4-fluorophenyl)-5-phenyl-pyrazolo[3,4-c]pyridazin-1-yl]-1-[(3R)-3-fluoropyrrolidin-1-yl]ethanone (Compound 1)

Step 1: N-(1H-pyrazol-5-yl)acetamide

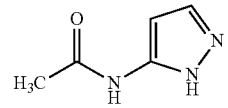

To a solution of 1H-pyrazol-5-amine (50 g, 0.602 mol) and N-methylmorpholine (160 mL, 1.44 mol) in CH$_2$Cl$_2$ (2 L) was added acetyl chloride (99 mL, 1.38 mol) dropwise at 0° C. under an atmosphere of nitrogen. The reaction mixture was stirred at room temperature for 1 d. Some di-acylated product was observed in an LCMS. The reaction mixture was concentrated in vacuo and the resulting solid was suspended in MeOH (2 L) and cooled to 0° C. 4 M NaOH solution (aq., 440 mL, 1.75 mol) was added slowly and the mixture allowed to warm to room temperature over 1.5 h. The MeOH was removed in vacuo and the solid was collected by filtration, washed with minimal cold water and dried in vacuo to provide the title compound as a solid (60 g).

Step 2: N-(4-iodo-1H-pyrazol-5-yl)acetamide

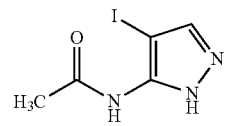

A suspension of N-(1H-pyrazol-5-yl)acetamide (60 g, 0.48 mol), iodic acid (21.1 g, 0.12 mol) and iodine (61 g, 0.24 mol) in ethanol (1.6 L) was heated at 60° C. for 1.5 h and cooled to room temperature. The reaction mixture was concentrated in vacuo and partitioned between ethyl acetate and 2 M Na$_2$S$_2$O$_3$ aq. solution. The layers were separated and the aqueous extracted with ethyl acetate. The combined organic layers were dried (MgSO$_4$), filtered and concentrated in vacuo to provide the title compound as a solid (105 g).

Step 3: N-(4-(phenylethynyl)-1H-pyrazol-5-yl)acetamide

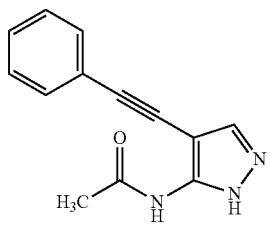 [SMILES: CC(=O)Nc1[nH]ncc1C#Cc1ccccc1]

Nitrogen was bubbled through a suspension of N-(4-iodo-1H-pyrazol-5-yl)acetamide (30 g, 120 mmol), 10% palladium on carbon (50% water, 7.4 g, 3 mmol), copper(I) iodide (1.14 g, 6 mmol), triphenylphosphine (6.3 g, 24 mmol) and triethylamine (50 mL, 360 mmol) in ethanol (600 mL) for 20 min. Phenyl acetylene (18.3 g, 179 mmol) was added and nitrogen bubbled through the mixture for a further 25 min. The reaction mixture was then heated and stirred under reflux conditions in an atmosphere of nitrogen for 3 d and cooled to room temperature. The reaction mixture was filtered through celite and the filtrate was concentrated in vacuo. The residue was purified by column chromatography (silica gel, isohexane/ethyl acetate 9:1 to 0:1) yielding the title compound as a solid (17.6 g).

Step 4: 1-(1-ethoxyethyl)-4-(phenylethynyl)-1H-pyrazol-5-amine

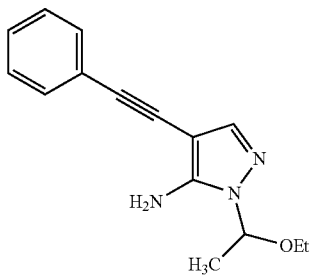 [SMILES: CCOC(C)n1ncc(C#Cc2ccccc2)c1N]

A solution of N-(4-(phenylethynyl)-1H-pyrazol-5-yl)acetamide (17.6 g, 78 mmol), ethoxyethene (11.2 mL, 117 mmol) and HCl in 1,4-dioxane (1 mL, 4 mmol) in CH$_2$Cl$_2$ (520 mL) was stirred at room temperature for 1 h and concentrated in vacuo. The residue was dissolved in ethanol (260 mL) and 25% aq. NaOH solution (260 mL) and the reaction mixture was heated to 75° C. for 4 h and cooled to room temperature. The ethanol was partly concentrated in vacuo and the resulting solid collected by filtration, washed with water and minimum cold ethanol and dried in vacuo to provide the title compound as a solid (16 g).

Step 5: 4-chloro-5-phenyl-1H-pyrazolo[3,4-c]pyridazine

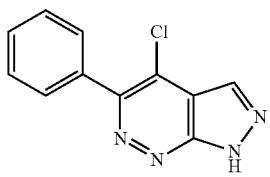 [SMILES: Clc1c(-c2ccccc2)nnc2[nH]ncc12]

Sodium nitrite (4.3 g, 63 mmol) was added to conc. HCl (314 mL) at −15° C. and stirred for 10 min. 1-(1-ethoxyethyl)-4-(phenylethynyl)-1H-pyrazol-5-amine (3 g, 31.4 mmol) was added and the mixture stirred at −10° C. for 10 min and room temperature for 1 d. The reaction mixture was cooled to 0° C. and CH$_2$Cl$_2$ (250 mL) was added. Under vigorous stirring, Na$_2$CO$_3$ (160 g) was added carefully followed by sat. aq. NaHCO$_3$ solution over a period of 2 h until the pH was 7 and there was no more foaming on further addition of base. The layers were separated and the aqueous phase was extracted with CH$_2$Cl$_2$. The combined organic layers were dried (MgSO$_4$), filtered and concentrated in vacuo. The residue was purified by column chromatography (silica gel, isohexane/diethyl ether 1:0 to 0:1) yielding the title compound as a solid (3.43 g).

Step 6: 4-chloro-3-iodo-5-phenyl-1H-pyrazolo[3,4-c]pyridazine

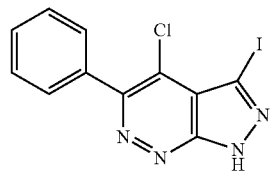 [SMILES: Clc1c(-c2ccccc2)nnc2[nH]nc(I)c12]

A suspension of 4-chloro-5-phenyl-1H-pyrazolo[3,4-c]pyridazine (2.44 g, 10.6 mmol) and N-iodosuccinimide (3.58 g, 15.9 mmol) in acetonitrile (106 mL) was heated at reflux for 1 d. The yellow solid was collected by filtration while warm to provide a mixture of the title compound and starting material (9:1, 4 g).

Step 7: 2-(4-chloro-3-iodo-5-phenyl-pyrazolo[3,4-c]pyridazin-1-yl)-1-[(3R)-3-fluoropyrrolidin-1-yl]ethanone

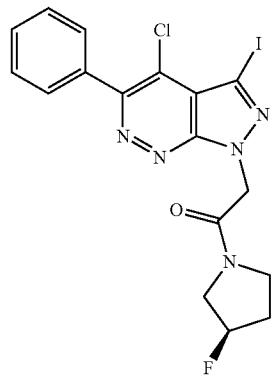 [SMILES: O=C(Cn1nc(I)c2c(Cl)c(-c3ccccc3)nnc21)N1CC[C@@H](F)C1]

Chloroacetyl chloride (632 µl, 7.94 mmol) was added dropwise to a solution of (3R)-3-fluoropyrrolidine (1 g, 7.94 mmol) and triethylamine (2.2 mL, 15.9 mmol) in CH$_2$Cl$_2$ (20 mL) at 5° C. The reaction mixture was stirred at room temperature for 1 h. Water and CH$_2$Cl$_2$ were added. The layers were separated and the aqueous was extracted with CH$_2$Cl$_2$. The combined organics were dried (MgSO$_4$), filtered and concentrated in vacuo, to yield 2-chloro-1-[(3R)-3-fluoropyrrolidin-1-yl]ethanone (4.7 g).

Sodium hydride (60% in mineral oil, 240 mg, 6 mmol) was added to a solution of 4-chloro-3-iodo-5-phenyl-1H-pyrazolo[3,4-c]pyridazine (1.06 g, 3 mmol) and 2-chloro-1-[(3R)-3-fluoropyrrolidin-1-yl]ethanone (740 mg, 4.5 mmol) in dry DMF (20 mL) at room temperature. The reaction mixture was stirred at room temperature for 16 h. 4% LiCl aq. solution and ethyl acetate was added. The layers were separated and the aqueous was extracted with ethyl acetate. The combined organics were dried (MgSO$_4$), filtered and concentrated in vacuo. The residue was partially purified by column chromatography (silica gel, isohexane/ethyl acetate 1:0 to 3:7). The resulting solid was dissolved in minimum CH$_2$Cl$_2$ and diethyl ether was added until a solid precipitated. The solid was collected by filtration to provide the title compound as a solid (846 mg).

Step 8: 2-[4-chloro-3-(4-fluorophenyl)-5-phenyl-pyrazolo[3,4-c]pyridazin-1-yl]-1-[(3R)-3-fluoropyrrolidin-1-yl]ethanone (Compound 1)

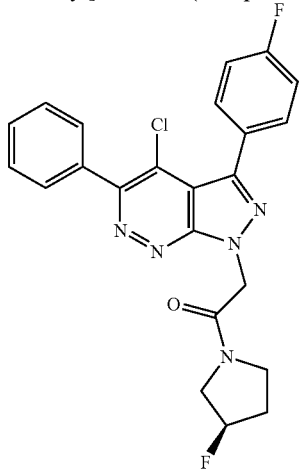 [SMILES: O=C(Cn1nc(-c2ccc(F)cc2)c2c(Cl)c(-c3ccccc3)nnc21)N1CC[C@@H](F)C1]

Nitrogen was bubbled through a suspension of 2-(4-chloro-3-iodo-5-phenyl-pyrazolo[3,4-c]pyridazin-1-yl)-1-[(3R)-3-fluoropyrrolidin-1-yl]ethanone (70 mg, 0.144 mmol), 4-fluorophenylboronic acid (22 mg, 0.158 mmol) and K$_3$PO$_4$ (92 mg, 0.43 mmol) in DMF (1.1 mL) and water (0.4 mL) for 20 min. 1,1'-Bis(diphenylphosphino)ferrocene-palladium(II)dichloride dichloromethane complex (12 mg, 0.014 mmol) was added and the tube sealed and heated using microwave irradiation to 60° C. for 30 min. The crude reaction mixture was filtered and partially purified by preparative HPLC. The residue was purified by chromatography (silica gel, isohexane/ethyl acetate 1:0 to 7:3) to provide Compound 1 (20 mg).
$^1$H NMR δ (ppm)(CHCl$_3$-d): 7.82-7.72 (4H, m), 7.55-7.47 (3H, m), 7.22-7.13 (2H, m), 5.68-5.52 (2H, m), 5.50-5.20 (1H, m), 4.00-3.79 (3H, m), 3.68-3.57 (1H, m), 2.49-2.27 (2H, m).
LCMS (10 cm_ESCI_Bicarb_MeCN) Rt 3.97 min; m/z 454 [M+H] 99.6% purity.

Example 2

2-[4-chloro-3-(3,4-difluorophenyl)-5-phenyl-pyrazolo[3,4-c]pyridazin-1-yl]-1-[(3R)-3-fluoropyrrolidin-1-yl]ethanone (Compound 2)

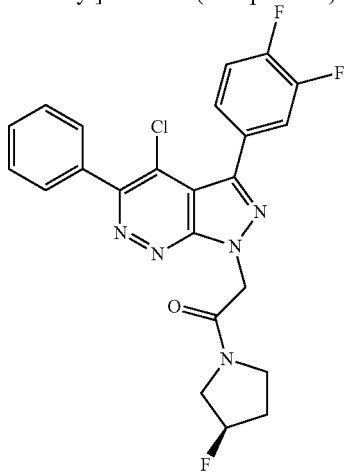

Compound 2 was synthesised according to Example 1, but using 3,4-difluorophenylboronic acid instead of 4-fluorophenylboronic acid in Step 8.
$^1$H NMR δ (ppm)(CHCl$_3$-d): 7.75-7.72 (2H, m), 7.68-7.62 (1H, m), 7.57-7.48 (4H, m), 7.34-7.30 (1H, m), 5.70-5.53 (2H, m), 5.46-5.19 (1H, m), 3.98-3.81 (3H, m), 3.65-3.58 (1H, m), 2.50-2.00 (2H, m).
LCMS (15 cm_Formic_ASCENTIS_HPLC_CH3CN) Rt 10.32 min; m/z 472 [M+H] 99.6% purity.

Example 3

2-[4-chloro-3-(2,5-difluorophenyl)-5-phenyl-pyrazolo[3,4-c]pyridazin-1-yl]-1-[(3R)-3-fluoropyrrolidin-1-yl]ethanone (Compound 3)

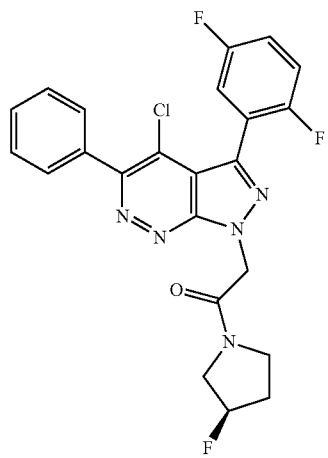 [SMILES: O=C(Cn1nc(-c2cc(F)ccc2F)c2c(Cl)c(-c3ccccc3)nnc21)N1CC[C@@H](F)C1]

Compound 3 was synthesised according to Example 1, but using 2,5-difluorophenylboronic acid instead of 4-fluorophenylboronic acid in Step 8.
$^1$H NMR δ (ppm)(CHCl$_3$-d): 7.78-7.74 (2H, m), 7.55-7.47 (3H, m), 7.38-7.33 (1H, m), 7.19-7.14 (2H, m), 5.68-5.53 (2H, m), 5.39-5.33 (1H, m), 4.00-3.81 (3H, m), 3.65-3.55 (1H, m), 2.50-2.00 (2H, m).
LCMS (15 cm_Bicarb_GeminiNX_HPLC_CH3CN) Rt 10.51 min; m/z 472 [M+H] 93.72% purity.

Example 4

2-[4-chloro-3-(2,3-difluorophenyl)-5-phenyl-pyrazolo[3,4-c]pyridazin-1-yl]-1-[(3R)-3-fluoropyrrolidin-1-yl]ethanone (Compound 4)

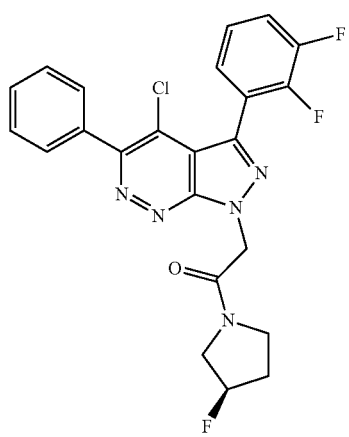 [SMILES: O=C(Cn1nc(-c2cccc(F)c2F)c2c(Cl)c(-c3ccccc3)nnc21)N1CC[C@@H](F)C1]

Compound 4 was synthesised according to Example 1, but using 2,3-difluorophenylboronic acid instead of 4-fluorophenylboronic acid in Step 8.

$^1$H NMR δ (ppm)(CHCl$_3$-d): 7.77-7.74 (2H, m), 7.54-7.47 (3H, m), 7.43-7.37 (1H, m), 7.33-7.29 (1H, m), 7.24-7.17 (1H, m), 5.69-5.54 (2H, m), 5.41-5.25 (1H, m), 4.01-3.78 (3H, m), 3.65-3.58 (1H, m), 2.00 (2H, m).

LCMS (15 cm_Bicarb_GeminiNX_HPLC_CH3CN) Rt 10.52 min; m/z 472 [M+H] 95.5% purity.

Example 5

4-chloro-3-(2,3-difluorophenyl)-1-[2-(4-methylpiperazin-1-yl)ethyl]-5-phenyl-pyrazolo[3,4-c]pyridazine (Compound 5)

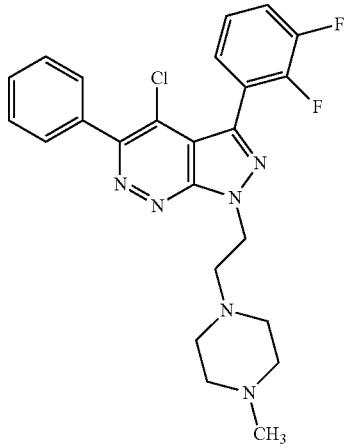 [SMILES: CN1CCN(CCn2nc(-c3cccc(F)c3F)c3c(Cl)c(-c4ccccc4)nnc32)CC1]

A solution of 4-chloro-3-iodo-5-phenyl-1H-pyrazolo[3,4-c]pyridazine and 4-chloro-5-phenyl-1H-pyrazolo[3,4-c]pyridazine (9:1, 1.4 g), 2-(4-methylpiperazin-1-yl)ethanol (1.13 g, 7.8 mmol), diethyl azodicarboxylate (1.37 g, 7.8 mmol) and triphenyl phosphine (2.07 g, 7.9 mmol) in 1,4-dioxane (26 mL) was heated to 85° C. for 1 h and then cooled to room temperature and concentrated in vacuo. The residue was partially purified by column chromatography (silica gel, starting with isohexane/ethyl acetate 1:0 to 0:1 then ethyl acetate/4 M NH$_3$ in MeOH 1:0 to 9:1) to provide 4-chloro-3-iodo-1-(2-(4-methylpiperazin-1-yl)ethyl)-5-phenyl-1H pyrazolo[3,4c]pyridazine (761 mg).

Compound 5 was synthesised according to Example 1, but using 2,3-difluorophenylboronic acid instead of 4-fluorophenylboronic acid and 4-chloro-3-iodo-1-(2-(4-methylpiperazin-1-yl)ethyl)-5-phenyl-1H pyrazolo[3,4c]pyridazine instead of 2-(4-chloro-3-iodo-5-phenyl-pyrazolo[3,4-c]pyridazin-1-yl)-1-[(3R)-3-fluoropyrrolidin-1-yl]ethanone in Step 8. Preparative HPLC yielded Compound 5 as a diformate salt.

$^1$H NMR δ (ppm) (DMSO-d$_6$): 8.18 (2H, s), 7.68-7.64 (2H, m), 7.62-7.54 (1H, m), 7.54-7.40 (4H, m), 7.37-7.30 (1H, m), 4.85 (2H, t), 2.89 (2H, t), 2.44 (4H, bs), 2.13 (4H, bs), 2.02 (3H, bs).

LCMS (10 cm_Formic_ACE 3 C18 AR_HPLC_CH3CN) Rt 9.94 min; m/z 469 [M+H] 95.98% purity.

Example 6

2-[4-chloro-3-(2-fluorophenyl)-5-phenyl-pyrazolo[3,4-c]pyridazin-1-yl]-1-pyrolidin-1-yl-ethanone (Compound 6)

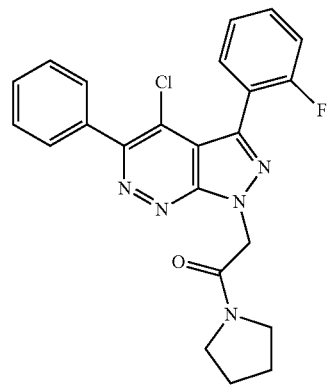 [SMILES: O=C(Cn1nc(-c2ccccc2F)c2c(Cl)c(-c3ccccc3)nnc21)N1CCCC1]

Sodium hydride (60% in mineral oil, 32 mg, 1.75 mmol) was added to a solution of 4-chloro-3-iodo-5-phenyl-1H-pyrazolo[3,4-c]pyridazine (400 mg, 1.12 mmol) and 2-chloro-1-(pyrrolidin-1-yl)ethanone (54 mg, 1.8 mmol) in dry DMF (7.5 mL) at room temperature. After 1.5 h at room temperature further sodium hydride (60% in mineral oil, 27 mg) was added and the suspension stirred for 2 h. 4% LiCl aq. solution and ethyl acetate was added. The layers were separated and the aqueous was extracted with ethyl acetate. The combined organics were dried (MgSO$_4$), filtered and concentrated in vacuo. The residue was partially purified by column chromatography (silica gel, isohexane/ethyl acetate 1:0 to 0:1). The resulting solid was dissolved in minimum CH$_2$Cl$_2$ and diethyl ether was added until a solid precipitated. The solid was collected by filtration to provide 2-(4-chloro-3-iodo-5-phenyl-1H-pyrazolo[3,4-c]pyridazin-1-yl)-1-(pyrrolidin-1-yl)ethanone (246 mg).

Compound 6 was synthesised according to Example 1, but using 2-fluorophenylboronic acid instead of 4-fluorophenylboronic acid and 2-(4-chloro-3-iodo-5-phenyl-1H-pyrazolo[3,4-c]pyridazin-1-yl)-1-(pyrrolidin-1-yl)ethanone instead of 2-(4-chloro-3-iodo-5-phenyl-pyrazolo[3,4-c]pyridazin-1-yl)-1-[(3R)-3-fluoropyrrolidin-1-yl]ethanone in Step 8.

$^1$H NMR δ (ppm)(CHCl$_3$-d): 7.77-7.74 (2H, m), 7.66-7.61 (1H, m), 7.53-7.45 (4H, m), 5.58 (2H, s), 3.66 (2H, t), 3.54 (2H, t), 2.11-2.05 (2H, m), 1.96-1.90 (2H, m).

LCMS (15 cm_Bicarb_GeminiNX_HPLC_CH3CN) Rt 10.62 min; m/z 436 [M+H] 95.36% purity.

Example 7

Synthesis scheme for 4-chloro-3,5-diphenyl-1H-pyrazolo[3,4-c]pyridazine

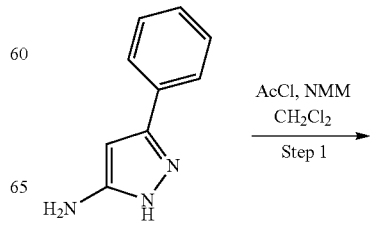

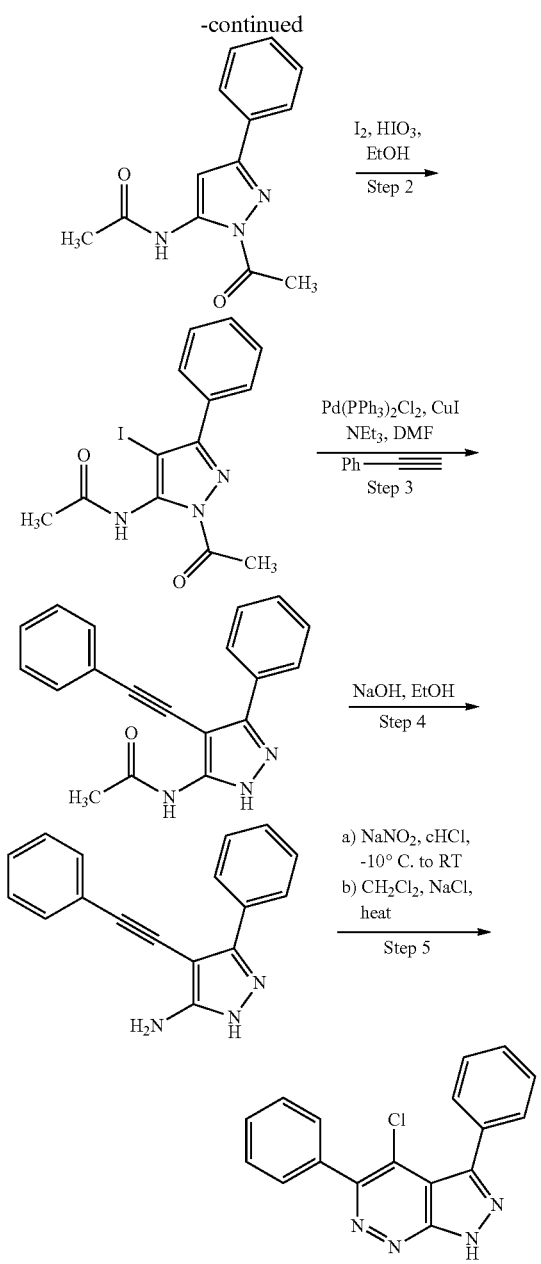

Step 1: N-(2-acetyl-5-phenyl-pyrazol-3-yl)acetamide

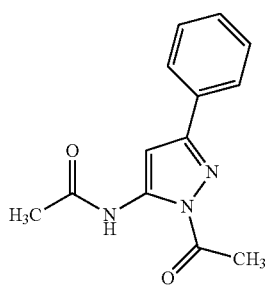 [SMILES: CC(=O)Nc1cc(-c2ccccc2)nn1C(C)=O]

To a solution of 5-phenyl-1H-pyrazol-3-amine (18.6 g, 0.117 mol) and N-methylmorpholine (30.8 mL, 0.281 mol) in CH₂Cl₂ (250 mL) was added acetyl chloride (20 mL, 0.281 mol) dropwise at 0° C. under an atmosphere of nitrogen. The reaction mixture was stirred at room temperature for 3 h. The reaction mixture was diluted with CH₂Cl₂ and water. The layers were separated and the organic layer was washed with water and brine, dried (phase separator cartridge) and concentrated in vacuo. Diethyl ether was added to the residue and the solid was collected by filtration, yielding the title compound as a solid (25.1 g).

Step 2: N-(2-acetyl-4-iodo-5-phenyl-pyrazol-3-yl)acetamide

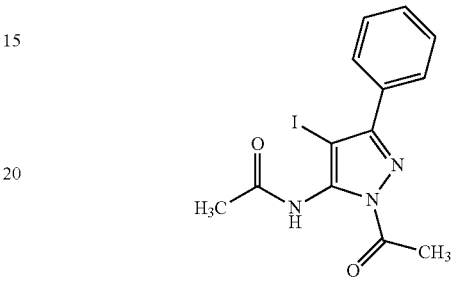

A suspension of N-(2-acetyl-5-phenyl-pyrazol-3-yl)acetamide (25.1 g, 0.103 mol), iodic acid (4.5 g, 0.026 mol) and iodine (15.7 g, 0.062 mol) in ethanol (250 mL) was heated at 50° C. for 3 h and cooled to room temperature. The reaction mixture was concentrated in vacuo and partitioned between CH₂Cl₂ and 2 M Na₂S₂O₃ aq. solution. The layers were separated and the organic washed with brine, dried (phase separator cartridge), and concentrated in vacuo to provide a mixture of the title compound and starting material (2.2:1, 30.3 g). The mixture was put in reaction again using iodic acid (1.6 g, 9.6 mmol) and iodine (9.7 g, 38 mmol) in ethanol (250 mL) under the same conditions, to provide the title compound as a solid (31.9 g).

Step 3: N-[3-phenyl-4-(2-phenylethynyl)-1H-pyrazol-5-yl]acetamide

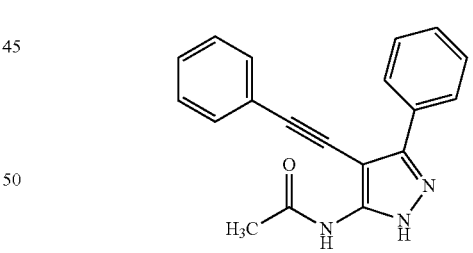

Nitrogen was bubbled through a mixture of N-(2-acetyl-4-iodo-5-phenyl-pyrazol-3-yl)acetamide (31.87 g, 86.4 mmol), phenyl acetylene (17.6 g, 173 mmol), triethylamine (200 mL) and DMF (100 mL) for 15 min. Copper iodide (1.64 g, 8.6 mmol) and bis(triphenylphosphine)palladium(II) dichloride (3.0 g, 4.3 mmol) were added and the reaction mixture was stirred at 90° C. under nitrogen for 3 h. The reaction mixture was cooled to room temperature, diluted with ethyl acetate and water. The organic phase was washed with water and brine, dried (MgSO₄), filtered and concentrated in vacuo. The residue was purified by column chromatography (silica gel, isohexane/ethyl acetate 5:1 to 1:1) yielding the title compound as a solid (12.5 g).

Step 4:
3-phenyl-4-(2-phenylethynyl)-1H-pyrazol-5-amine

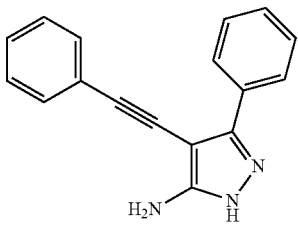 [SMILES: Nc1[nH]nc(-c2ccccc2)c1C#Cc1ccccc1]

A mixture of N-[3-phenyl-4-(2-phenylethynyl)-1H-pyrazol-5-yl]acetamide (12.5 g, 42 mmol), ethanol (100 mL) and 25% aq. NaOH solution (100 mL) was stirred and heated to 90° C. for 1 h and cooled to room temperature. The reaction mixture was diluted with ethyl acetate and water. The organic phase was washed with water and brine, dried (phase separator cartridge) and concentrated in vacuo. Diethyl ether was added to the residue and the solid was collected by filtration, washed with diethyl ether and dried in vacuo to provide the title compound as a solid (5.4 g).

Step 5:
4-chloro-3,5-diphenyl-1H-pyrazolo[3,4-c]pyridazine

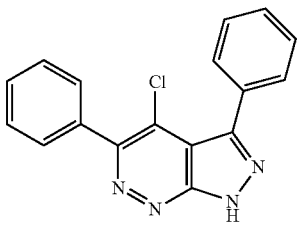 [SMILES: Clc1c(-c2ccccc2)nnc2[nH]nc(-c3ccccc3)c12]

Sodium nitrite (2.88 g, 42 mmol) was added portionwise to cHCl (314 mL) at −15° C. and stirred for 15 min. 3-phenyl-4-(2-phenylethynyl)-1H-pyrazol-5-amine (5.4 g, 21 mmol) was added as a solid, followed by the addition of CH$_2$Cl$_2$ (10 mL). The reaction mixture was allowed to warm up and stirred at room temperature for 1 h. The reaction mixture was diluted with CH$_2$Cl$_2$ (44 mL) and NaCl (2.7 g) was added. The reaction mixture was heated to 50° C. for 1 d. The layers were separated and the organic layer was washed with water, dried (phase separator cartridge) and concentrated in vacuo. The residue was purified by column chromatography (silica gel, isohexane/ethyl acetate 4:1, then CH$_2$Cl$_2$/ethyl acetate 1:0 to 4:1) yielding the title compound as a solid (3.0 g).

Example 8

Synthesis scheme for 4-chloro-3-(3-fluorophenyl)-5-phenyl-M-pyrazolo[3,4-c]pyridazine

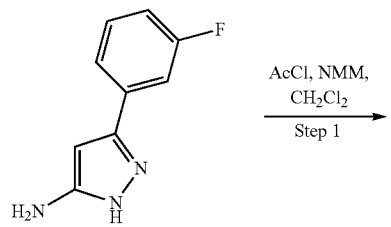

Step 1:
N-[3-(3-fluorophenyl)-1H-pyrazol-5-yl]acetamide

To a solution of 3-(3-fluorophenyl)-1H-pyrazol-5-amine (6.5 g, 36 mmol) and N-methylmorpholine (9.7 mL, 88 mmol) in CH$_2$Cl$_2$ (150 mL) was added acetyl chloride (6 mL, 85 mmol) dropwise at 0° C. under an atmosphere of nitrogen. The reaction mixture was stirred at room temperature for 1 d. The reaction mixture was concentrated in vacuo. MeOH (50 mL) and THF (50 mL) were added to the residue, followed by the addition of NaOH solution (aq. 2.5 M, 42.5 mL) at 0° C. The reaction mixture was stirred at room temperature for 15 min and HCl solution was added until pH reached ~6. The organic solvents were evaporated in vacuo. The solid from the resulting aqueous suspension was collected by filtration, yielding the title compound as a solid (7.6 g).

Step 2: N-[3-(3-fluorophenyl)-4-iodo-1H-pyrazol-5-yl]acetamide

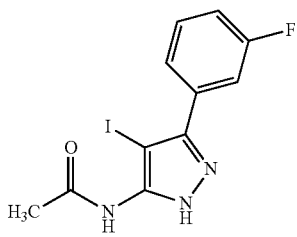 [SMILES: CC(=O)Nc1[nH]nc(-c2cccc(F)c2)c1I]

A suspension of N-[3-(3-fluorophenyl)-1H-pyrazol-5-yl]acetamide (7.6 g, 34.7 mmol), iodic acid (1.5 g, 8.5 mmol) and iodine (4.4 g, 17.3 mmol) in ethanol (200 mL) was heated at 60° C. for 1 h and cooled to room temperature. The reaction mixture was concentrated in vacuo and partitioned between $CH_2Cl_2$ and 2 M $Na_2S_2O_3$ aq. solution. The layers were separated and the organic washed with brine, dried ($MgSO_4$), and concentrated in vacuo to provide the title compound as a solid (10.8 g).

Step 3: N-[3-(3-fluorophenyl)-4-(2-phenylethynyl)-1H-pyrazol-5-yl]acetamide

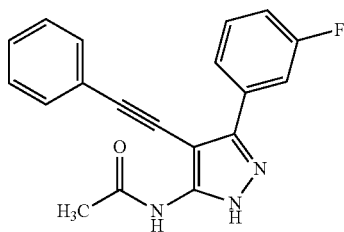 [SMILES: CC(=O)Nc1[nH]nc(-c2cccc(F)c2)c1C#Cc1ccccc1]

Nitrogen was bubbled through a mixture of N-[3-(3-fluorophenyl)-4-iodo-1H-pyrazol-5-yl]acetamide (10.8 g, 44 mmol), phenyl acetylene (12.5 g, 123 mmol), triethylamine (100 mL) and DMF (40 mL) for 15 min. Copper iodide (840 mg, 4.42 mmol) and bis(triphenylphosphine)palladium(II) dichloride (1.5 g, 2.1 mmol) were added and the reaction mixture was stirred at 90° C. under nitrogen for 6 h. The reaction mixture was cooled to room temperature, diluted with ethyl acetate and water. The organic phase was washed with water and brine, dried ($MgSO_4$), filtered and concentrated in vacuo. The residue was purified by column chromatography (silica gel, isohexane/ethyl acetate 1:0 to 0:1) yielding the title compound as a solid (4 g).

Step 4: 3-(3-fluorophenyl)-4-(2-phenylethynyl)-1H-pyrazol-5-amine

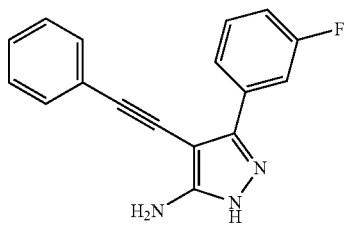 [SMILES: Nc1[nH]nc(-c2cccc(F)c2)c1C#Cc1ccccc1]

A mixture of N-[3-(3-fluorophenyl)-4-(2-phenylethynyl)-1H-pyrazol-5-yl]acetamide (2 g, 6.2 mmol), ethanol (22 mL) and 25% aq. NaOH solution (22 mL) was stirred and heated to 80° C. for 1 h and cooled to room temperature. The reaction mixture was diluted with ethyl acetate and water. The organic phase was washed with water and brine, dried (phase separator cartridge) and concentrated in vacuo, to provide the title compound as a solid (1.2 g).

Step 5: 4-chloro-3-(3-fluorophenyl)-5-phenyl-1H-pyrazolo[3,4-c]pyridazine

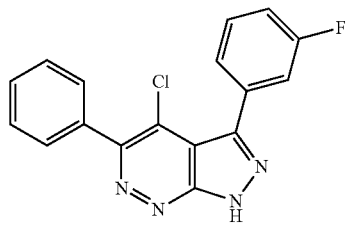 [SMILES: Fc1cccc(-c2n[nH]c3nnc(-c4ccccc4)c(Cl)c23)c1]

Sodium nitrite (740 mg, 10.7 mmol) was added portionwise to cHCl (24 mL) at −15° C. and stirred for 15 min. 3-(3-fluorophenyl)-4-(2-phenylethynyl)-1H-pyrazol-5-amine (1 g, 3.6 mmol) was added as a solid, followed by the addition of $CH_2Cl_2$ (10 mL). The reaction mixture was allowed to warm up and stirred at room temperature for 1.5 h. The reaction mixture was diluted with $CH_2Cl_2$ (20 mL) and NaCl (0.5 g) was added. The reaction mixture was heated to 50° C. for 1 d. The layers were separated and the organic layer was washed with water, dried (phase separator cartridge) and concentrated in vacuo. The residue was purified by column chromatography (silica gel, ethyl acetate/isohexane 0:1 to 7:3) yielding the title compound as a solid (500 mg).

Example 9

4-chloro-1-(2-isopropoxyethyl)-3,5-diphenyl-pyrazolo[3,4-c]pyridazine (Compound 7)

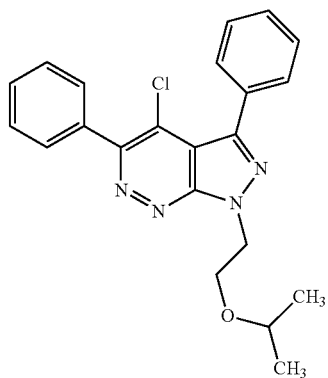 [SMILES: CC(C)OCCn1nc(-c2ccccc2)c2c(Cl)c(-c3ccccc3)nnc21]

A mixture of 4-chloro-3,5-diphenyl-1H-pyrazolo[3,4-c]pyridazine (0.33 mmol), 2-isopropoxyethanol (0.65 mmol), diethyl azodicarboxylate (114 mg, 0.65 mmol) and triphenylphosphine (171 mg, 0.65 mmol) in 1,4-dioxane (2 mL) was heated using microwave irradiation to a temperature between 85 and 120° C. for a 30 to 90 min period. The reaction mixture was concentrated in vacuo and the residue was purified by preparative HPLC to provide Compound 7.

$^1$H NMR δ (ppm)($CHCl_3$-d): 7.79-7.74 (4H, m), 7.55-7.44 (6H, m), 4.98 (2H, t), 4.08 (2H, t), 3.71-3.63 (1H, m), 1.10 (6H, t).

LCMS (10 cm_Formic_ACE 3 C18 AR_HPLC_CH3CN) Rt 13.18 min; m/z 393 [M+H] 93.65% purity.

Example 10

4-chloro-3-(3-fluorophenyl)-1-[2-(4-methylpiperazin-1-yl)ethyl]-5-phenyl-pyrazolo[3,4-c]pyridazine (Compound 8)

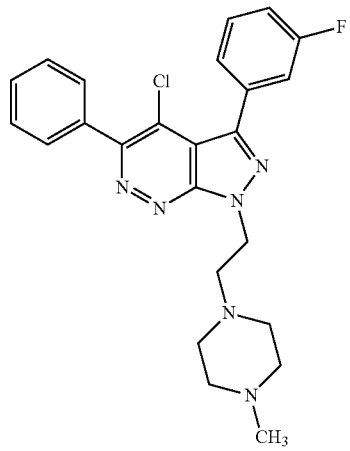 [SMILES: CN1CCN(CCn2nc(-c3cccc(F)c3)c3c(Cl)c(-c4ccccc4)nnc32)CC1]

A mixture of 4-chloro-3-(3-fluorophenyl)-5-phenyl-1H-pyrazolo[3,4-c]pyridazine (0.33 mmol), 2-(4-methylpiperazin-1-yl)ethanol (0.65 mmol), diethyl azodicarboxylate (114 mg, 0.65 mmol) and triphenyl phosphine (171 mg, 0.65 mmol) in 1,4-dioxane (2 mL) was heated using microwave irradiation to a temperature between 85 and 120° C. for a 30 to 90 min period. The reaction mixture was concentrated in vacuo and the residue was purified by preparative HPLC to provide Compound 8.

$^1$H NMR δ (ppm)(CHCl$_3$-d): 7.81-7.77 (2H, m), 7.57-7.44 (6H, m), 7.20-7.18 (1H, m), 4.95 (2H, t), 3.07 (2H, t), 2.65 (4H, bs), 2.35 (4H, bs), 2.25 (3H, s).

LCMS (10 cm_Formic_ACE 3 C18 AR_HPLC_CH3CN) Rt 9.93 min; m/z 451 [M+H] 99.18% purity.

Example 11

4-[2-[4-chloro-3-(3-fluorophenyl)-5-phenyl-pyrazolo[3,4-c]pyridazin-1-yl]ethyl]morpholine (Compound 9)

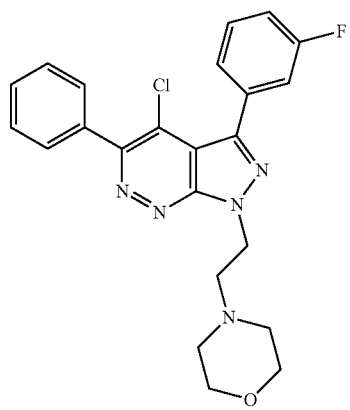 [SMILES: Fc1cccc(-c2nn(CCN3CCOCC3)c3nnc(-c4ccccc4)c(Cl)c23)c1]

A mixture of 4-chloro-3-(3-fluorophenyl)-5-phenyl-1H-pyrazolo[3,4-c]pyridazine (0.33 mmol), 2-morpholinoethanol (0.65 mmol), diethyl azodicarboxylate (114 mg, 0.65 mmol) and triphenyl phosphine (171 mg, 0.65 mmol) in 1,4-dioxane (2 mL) was heated using microwave irradiation to a temperature between 85 and 120° C. for a 30 to 90 min period. The reaction mixture was concentrated in vacuo and the residue was purified by preparative HPLC to provide Compound 9.

$^1$H NMR δ (ppm)(CHCl$_3$-d): 7.80-7.77 (2H, m), 7.60-7.45 (6H, m), 7.22-7.16 (1H, m), 4.95 (2H, t), 3.62 (4H, t), 3.06 (2H, t, 2.61 (4H, t).

LCMS (15 cm_Bicarb_GeminiNX_HPLC_CH3CN) Rt 11.16 min; m/z 438 [M+H] 97.23% purity.

Example 12

4-chloro-3-(3,4-difluorophenyl)-5 phenyl-1H-pyrazolo[3,4-c]pyridazine

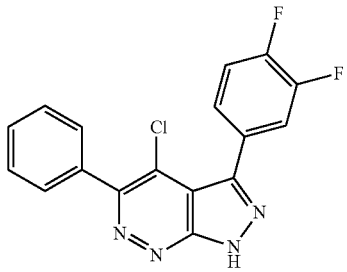 [SMILES: Fc1ccc(-c2n[nH]c3nnc(-c4ccccc4)c(Cl)c23)cc1F]

4-Chloro-3-(3,4-difluorophenyl)-5-phenyl-1H-pyrazolo[3,4-c]pyridazine was synthesized according to Example 8, but using 3-(3,4-difluorophenyl)-1H-pyrazol-5-amine instead of 3-(3-fluorophenyl)-1H-pyrazol-5-amine in step 1.

Example 13

4-chloro-3-(3,4-difluorophenyl)-1-[2-(4-methylpiperazin-1-yl)ethyl]-5-phenyl-pyrazolo[3,4-c]pyridazine (Compound 10)

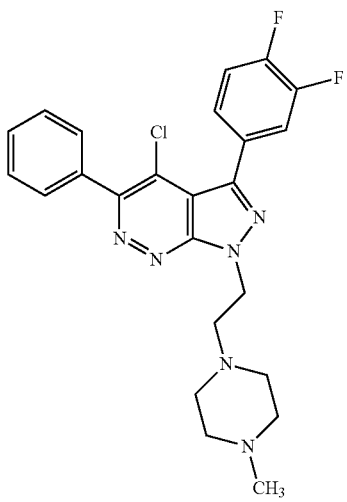 [SMILES: CN1CCN(CCn2nc(-c3ccc(F)c(F)c3)c3c(Cl)c(-c4ccccc4)nnc32)CC1]

A mixture of 4-chloro-3-(3,4-difluorophenyl)-5-phenyl-1H-pyrazolo[3,4-c]pyridazine (0.33 mmol), 2-(4-methylpiperazin-1-yl)ethanol (0.65 mmol), diethyl azodicarboxylate (114 mg, 0.65 mmol) and triphenyl phosphine (171 mg, 0.65 mmol) in 1,4-dioxane (2 mL) was heated using microwave irradiation to a temperature between 85 and 120° C. for a 30 to 90 min period. The reaction mixture was concentrated in vacuo and the residue was purified by preparative HPLC to provide Compound 10.

$^1$H NMR δ (ppm)(CHCl$_3$-d): 7.78-7.75 (2H, m), 7.65-7.59 (1H, m), 7.58-7.51 (4H, m), 7.33-7.29 (1H, m), 4.93 (2H, t), 3.16 (2H, t), 3.08 (4H, bs), 1.59 (4H, bs), 2.67 (3H, s).

LCMS (10 cm_ESCI_Bicarb_MeCN) Rt 4.27 min; m/z 469 [M+H] 96.02% purity.

Example 14

4-chloro-5-(3-fluorophenyl)-3-phenyl-1H-pyrazolo[3,4-c]pyridazine

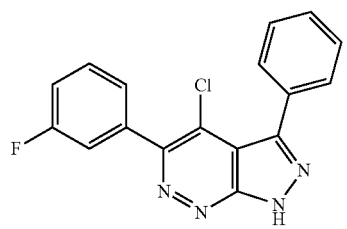 [SMILES: Fc1cccc(-c2nnc3[nH]nc(-c4ccccc4)c3c2Cl)c1]

4-Chloro-5-(3-fluorophenyl)-3-phenyl-1H-pyrazolo[3,4-c]pyridazine was synthesised according to Example 7, but using 3-fluorophenyl acetylene instead of phenyl acetylene in Step 3.

Example 15

2-[4-chloro-5-(3-fluorophenyl)-3-phenyl-pyrazolo[3,4-c]pyridazin-1-yl]-1-pyrrolidin-1-yl-ethanone (Compound 11)

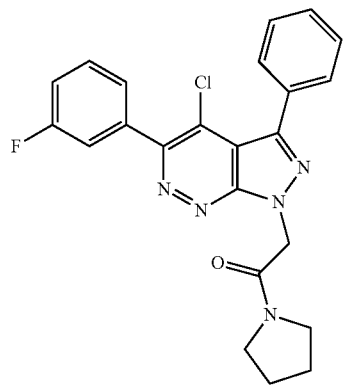 [SMILES: O=C(Cn1nc(-c2ccccc2)c2c(Cl)c(-c3cccc(F)c3)nnc21)N1CCCC1]

A mixture of 4-chloro-5-(3-fluorophenyl)-3-phenyl-1H-pyrazolo[3,4-c]pyridazine (0.33 mmol), 2-hydroxy-1-(pyrrolidin-1-yl)ethanone (0.65 mmol), diethyl azodicarboxylate (114 mg, 0.65 mmol) and triphenyl phosphine (171 mg, 0.65 mmol) in 1,4-dioxane (2 mL) was heated using microwave irradiation to a temperature between 85 and 120° C. for a 30 to 90 min period. The reaction mixture was concentrated in vacuo and the residue was purified by preparative HPLC to provide Compound 11.

$^1$H NMR δ (ppm)(CHCl$_3$-d): 7.81-7.76 (2H, m), 7.55-7.45 (6H, m), 7.23-7.15 (1H, m), 5.58 (2H, s), 3.67 (2H, t), 3.54 (2H, t), 2.13-2.05 (2H, m), 1.97-1.89 (2H, m).

LCMS (10 cm_ESCI_Bicarb_MeCN) Rt 3.69 min; m/z 436 [M+H] 98.67% purity.

Example 16 isobutyl 2-(4-chloro-3,5-diphenyl-pyrazolo[3,4-c]pyridazin-1-yl)acetate (Compound 12)

Synthesis scheme for isobutyl 2-(4-chloro-3,5-diphenyl-pyrazolo[3,4-c]pyridazin-1-yl)acetate

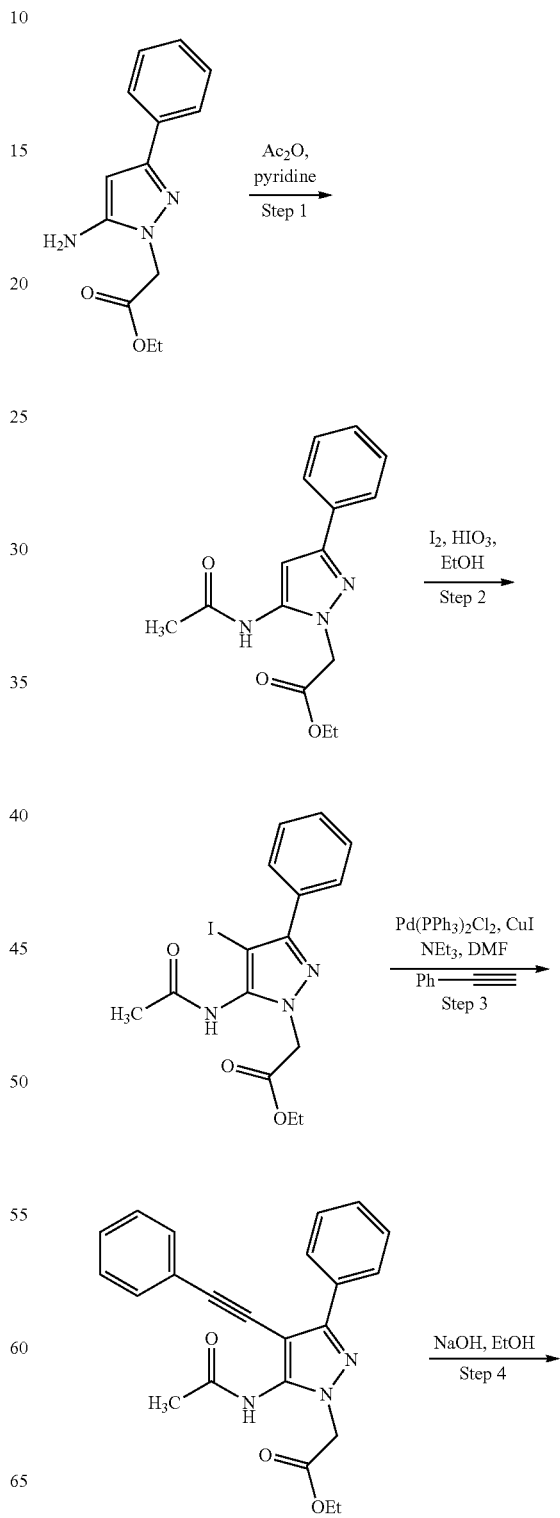

solid (22 g). The mother liquors were concentrated in vacuo and washed with cold CH$_2$Cl$_2$ to yield a second batch of 15 g.

Step 2: ethyl 2-(5-acetamido-4-iodo-3-phenyl-pyrazol-1-yl)acetate

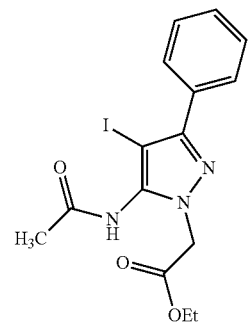 [SMILES: CCOC(=O)Cn1nc(-c2ccccc2)c(I)c1NC(C)=O]

A suspension of ethyl 2-(5-acetamido-3-phenyl-pyrazol-1-yl)acetate (37 g, 129 mmol), iodic acid (5.6 g, 32 mmol) and iodine (19.7 g, 77 mmol) in ethanol (400 mL) was heated at 50° C. for 2 h and cooled to room temperature. The reaction mixture was concentrated in vacuo and the residue was eluted through a pad of silica gel with CH$_2$Cl$_2$ diethyl ether (1:0 to 97:3). The residue was partitioned between CH$_2$Cl$_2$ and 2 M Na$_2$S$_2$O$_3$ aq. solution. The layers were separated and the organic washed was dried (MgSO$_4$), and concentrated in vacuo to provide a residue that was partially purified by chromatography (silica gel, CH$_2$Cl$_2$/isohexane 1:1 to 1:0, then CH$_2$Cl$_2$/diethyl ether 9:1 to 8:2), then triturated with diethyl ether to provide the title compound as an off-white solid (43 g).

Step 3: ethyl 2-[5-acetamido-3-phenyl-4-(2-phenyl-ethynyl)pyrazol-1-yl]acetate

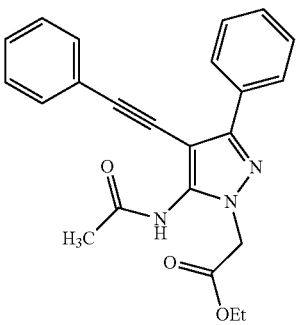 [SMILES: CCOC(=O)Cn1nc(-c2ccccc2)c(C#Cc2ccccc2)c1NC(C)=O]

Nitrogen was bubbled through a mixture of ethyl 2-(5-acetamido-4-iodo-3-phenyl-pyrazol-1-yl)acetate (18.6 g, 45 mmol), phenyl acetylene (9.2 g, 90 mmol), copper iodide (860 mg, 4.5 mmol), triethylamine (200 mL) and DMF (75 mL) for 15 min. Bis(triphenylphosphine)palladium(II) dichloride (1.6 g, 2.25 mmol) was added and the reaction mixture was stirred at 90° C. under nitrogen for 4.5 h. The reaction mixture was cooled to room temperature, diluted with ethyl acetate and water. The organic phase was washed with water and brine, dried (MgSO$_4$), filtered and concentrated in vacuo. The residue was partially purified by column chromatography (silica gel, CH$_2$Cl$_2$, then isohexane/ethyl

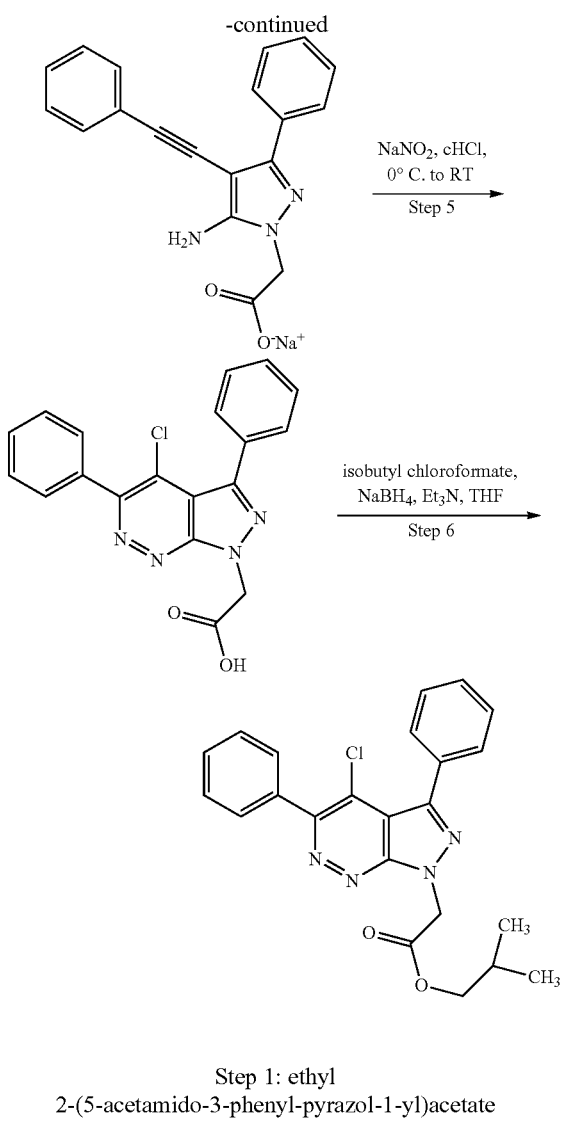

Step 1: ethyl 2-(5-acetamido-3-phenyl-pyrazol-1-yl)acetate

To a solution of ethyl 2-(5-amino-3-phenyl-pyrazol-1-yl)acetate (49 g, 0.17 mol) in pyridine (200 mL) was added acetic anhydride (17.4 g, 0.17 mol) dropwise at 0° C. under an atmosphere of nitrogen. The reaction mixture was stirred at room temperature for 16 h. The reaction mixture was concentrated in vacuo. The residue was diluted with CH$_2$Cl$_2$ and water. The layers were separated and the organic layer was washed with water and brine, dried (MgSO$_4$) and concentrated in vacuo. CH$_2$Cl$_2$ was added to the residue and the solid was collected by filtration, yielding the title compound as a acetate 1:1 followed by CH₂Cl₂/ethyl acetate 9:1 to 8:2), then triturated with diethyl ether to provide the title compound as a solid (13 g).

Step 4: sodium 2-[5-amino-3-phenyl-4-(2-phenyl-ethynyl)pyrazol-1-yl]acetate

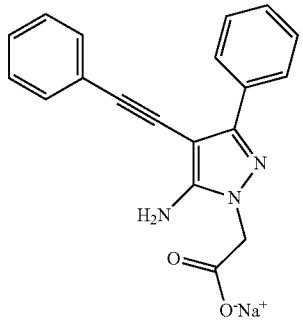

A mixture of ethyl 2-[5-acetamido-3-phenyl-4-(2-phenyl-ethynyl)pyrazol-1-yl]acetate (13 g, 34 mmol), ethanol (150 mL) and 25% aq. NaOH solution (150 mL) was stirred and heated to 80° C. for 8 h and cooled to room temperature. Upon cooling, a precipitate formed. The precipitate was filtered and washed with cooled mixture of ethyl acetate/water (1:1). The solid was further triturated with diethyl ether, filtered and dried to provide 9.8 g of the title compound.

Step 5: 2-(4-chloro-3,5-diphenyl-1Hpyrazolo[3,4-c]pyridazin-1-yl)acetic acid

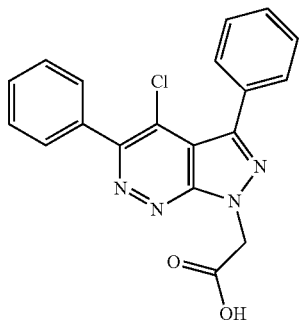 [SMILES: O=C(O)Cn1nc(-c2ccccc2)c2c(Cl)c(-c3ccccc3)nnc21]

Sodium nitrite (1.86 mg, 26.9 mmol) was added portionwise to cHCl (30 mL) at 0° C. and stirred for 15 min. Sodium 2-[5-amino-3-phenyl-4-(2-phenylethynyl)pyrazol-1-yl]acetate (3 g, 8.85 mmol) was added as a solid, portionwise. The suspension was then stirred at room temperature for 16 h. The reaction mixture was diluted with CH₂Cl₂ and washed with water and brine. The organic layer was dried (MgSO₄) and concentrated in vacuo. The residue was purified by column chromatography (silica gel, diethyl ether/CH₂Cl₂ 1:9) yielding the title compound as a solid (1.7 g).

Step 6: isobutyl 2-(4-chloro-3,5-diphenyl-pyrazolo [3,4-c]pyridazin-1-yl)acetate (Compound 12)

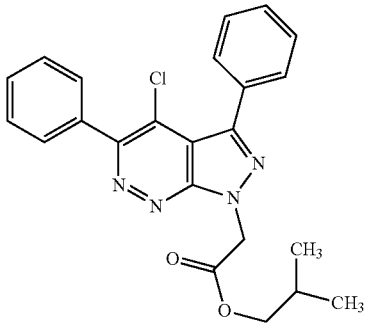 [SMILES: CC(C)COC(=O)Cn1nc(-c2ccccc2)c2c(Cl)c(-c3ccccc3)nnc21]

Triethylamine (535 μL, 3.8 mmol) was added to 2-(4-chloro-3,5-diphenyl-1Hpyrazolo[3,4-c]pyridazin-1-yl)acetic acid (700 mg, 1.92 mmol) in THF (20 mL) at 0° C., followed by the addition of isobutylchloroformate (342 mg, 2.9 mmol). The reaction mixture was stirred for 1 h. Sodium borohydride (220 mg, 5.8 mmol) was then added portionwise and the reaction mixture was stirred at room temperature for 3 h. The reaction mixture was diluted with 0.5 M HCl and the aqueous layer was extracted twice with ethyl acetate. The combined organic phases were washed with water and brine, dried (phase separator), and concentrated in vacuo. The residue was purified by chromatography (silica gel, ethyl acetate/isohexane 0:1 to 1:0), to provide Compound 12 as a solid (50 mg).

¹H NMR δ (ppm)(CHCl₃-d): 7.80-7.73 (4H, m), 7.56-7.48 (6H, m), 5.60 (2H, s), 3.99 (2H, d), 1.97-1.90 (1H, m), 0.90 (6H, d).

LCMS (10 cm_ESCI_Bicarb_MeCN) Rt 4.24 min; m/z 421 [M+H] 98.88% purity.

Example 17

4-Chloro-3-iodo-5-phenyl-1-(2-pyrrolidin-1-ylethyl) pyrazolo[3,4-c]pyridazine

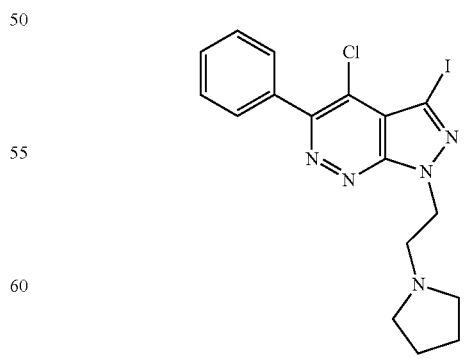

4-Chloro-3-iodo-5-phenyl-1-(2-pyrrolidin-1-ylethyl) pyrazolo[3,4-c]pyridazine was synthesised according to Example 1 through Step 6, but using 2-pyrrolidin-1-ylethanol in place of 2-chloro-1-[(3R)-3-fluoropyrrolidin-1-yl]ethanone in Step 7 to provide the title compound.

Example 18

4-Chloro-3,5-diphenyl-1-(2-pyrrolidin-1-ylethyl)pyrazolo[3,4-c]pyridazine (Compound 13)

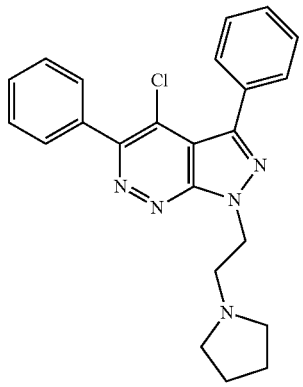 [SMILES: Clc1c(-c2ccccc2)nnc2c1c(-c1ccccc1)nn2CCN1CCCC1]

Compound 13 was synthesised according to Example 1, Step 8 using phenylboronic acid in place of 4-fluorophenylboronic acid and using 4-chloro-3-iodo-5-phenyl-1-(2-pyrrolidin-1-ylethyl)pyrazolo[3,4-c]pyridazine in place of 2-(4-chloro-3-iodo-5-phenyl-pyrazolo[3,4-c]pyridazin-1-yl)-1-[(3R)-3-fluoropyrrolidin-1-yl]ethanone.

$^1$H NMR δ (ppm)(CHCl$_3$-d): 7.79-7.76 (4H, m), 7.55-7.44 (6H, m), 4.97 (2H, t), 3.22 (2H, t), 2.68 (4H, bs), 1.88-1.65 (4H, m).

LCMS (10 cm_Formic_ACE 3 C18 AR_HPLC_CH3CN) Rt 9.98 min; m/z 404 [M+H] 95.91% purity.

Example 19

2-[4-chloro-3-(3-fluorophenyl)-5-phenyl-pyrazolo[3,4-c]pyridazin-1-yl]-1-[(3R)-3-fluoropyrrolidin-1-yl]ethanone (Compound 14)

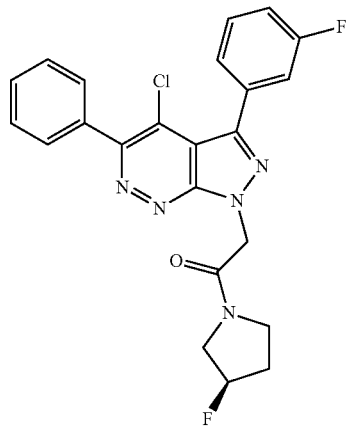 [SMILES: O=C(Cn1nc(-c2cccc(F)c2)c2c(Cl)c(-c3ccccc3)nnc21)N1CC[C@@H](F)C1]

Compound 14 was synthesised according to Example 1, Step 8 using 3-fluorophenylboronic acid instead of 4-fluorophenylboronic acid.

$^1$H NMR δ (ppm)(CHCl$_3$-d): 7.76-7.74 (2H, m), 7.61-7.59 (1H, m), 7.56-7.43 (5H, m), 7.18 (1H, m), 5.69-5.54 (2H, m), 5.36 (1H, m), 4.00-3.84 (3H, m), 3.62 (1H, m), 2.50-2.00 (2H, m).

LCMS (15 cm_Formic_ASCENTIS_HPLC_CH3CN) Rt 10.25 min; m/z 454 [M+H] 96.13% purity.

Example 20

Assay Method Showing Activity of Compounds of the Invention that Restore Expression of N48K Clarin-1 (24 Hour Incubation)

Clarin-1 is the protein encoded by the gene mutated in Usher III Syndrome (Adato et al., 2002). The most prevalent mutation in Clarin-1 in North America is N48K, which is reported to cause loss of glycosylation and a trafficking defect (Tian et al., 2009). As a consequence, the N48K protein does not reach the plasma membrane and is degraded by the proteasome. Thus it is believed that restoring the trafficking of N48K Clarin-1 to the cell surface provides an avenue of intervention for Usher III Syndrome.

A useful cellular model to demonstrate the utility of compounds of the invention that restore expression of N48K Clarin-1 is the HEK293-Clarin-1 N48K-HA D9 cell line (Tian et al., 2009). In a typical experiment, these cells were seeded on collagen-coated 96-well plates at a cell density of 20,000 cells per well in Dulbecco's Modified Eagle Medium (DMEM) contain 10% fetal bovine serum in a humidified incubator at 37° C., 5% $CO_2$. After an overnight incubation, compounds were added for a 24 hr incubation in DMEM medium contain 10% fetal bovine serum in a humidified incubator at 37° C., 5% $CO_2$. As a negative control, DMSO was used at 0.25% final concentrations. Compounds were typically tested in triplicate fashion. After the 24 hr incubation with compounds, the cells were fixed by the addition of 10% buffered formalin to the wells to achieve a final concentration of 4% formalin. After a 20 min fixation at room temperature, wells were washed three times with phosphate-buffered saline (PBS) containing Triton X-100 (0.02 phosphate, 150 mM NaCl, 0.1% Triton X-100).

The HA-tagged N48K Clarin-1 was detected with an antibody against the HA tag (HA.11 Clone 16B12 Monoclonal antibody, Covance #MMS-101P) at a dilution of 1:1000 in PBS containing Triton X-100. After a 90 min incubation, wells were washed three times with PBS containing Triton X-100, and a secondary antibody (Goat anti-mouse IgG-Cy3 (1.5 mg/ml), Jackson IR Europe #115165003) was added to the wells at a dilution of 1:250 in PBS containing Triton X-100 for 45 min. Wells were subsequently washed three times with PBS containing Triton X-100, and a final staining for nuclei was performed by the addition of DAPI (4',6-diamidino-2-phenylindole) at a dilution of 1:10,000. The imaging of the stained cells was performed on an InCell 1000 High Content Imager (GE Healthcare), reading out the Cy3 channel for N48K Clarin-1 and the DAPI channel for nuclei. The images were analyzed and quantitated using a specific algorithm. This algorithm measured the HA-Clarin-1 staining for each cell based on the additional nuclear segmentation of the DAPI signal (FIG. 1). This algorithm measured the intensity per cell, and thus it is less sensitive for variation in cell number. Per well, approximately 2,000 cells were measured to achieve an average density per cell measurement.

Example 21

An Assay Method Showing Activity of Compounds of the Invention that Restore Expression of N48K Clarin-1 (2 Hour Incubation)

Clarin-1 is the protein encoded by the gene mutated in Usher III Syndrome (Adato et al., 2002). The most prevalent mutation in Clarin-1 in North America is N48K, which is reported to cause loss of glycosylation and a trafficking defect (Tian et al., 2009). As a consequence, the N48K protein does not reach the plasma membrane and is degraded by the proteasome. Thus it is believed that restoring the trafficking of N48K Clarin-1 to the cell surface provides an avenue of intervention for Usher III Syndrome.

A useful cellular model to demonstrate the utility of compounds of the invention that restore expression of N48K Clarin-1 is the HEK293-Clarin-1 N48K-HA D9 cell line (Tian et al., 2009). In a typical experiment, these cells were seeded on collagen-coated 96-well plates at a cell density of 20,000 cells per well in Dulbecco's Modified Eagle Medium (DMEM) contain 10% fetal bovine serum in a humidified incubator at 37° C., 5% $CO_2$. After an overnight incubation, compounds were added for a 2 hr incubation in DMEM medium contain 10% fetal bovine serum in a humidified incubator at 37° C., 5% $CO_2$. As a negative control, DMSO was used at 0.25% final concentrations. Compounds were typically tested in triplicate fashion. After the 2 hr incubation with compounds, the cells were incubated in fresh medium for 22 hr. The cells were then fixed by the addition of 10% buffered formalin to the wells to achieve a final concentration of 4% formalin. After a 20 min fixation at room temperature, wells were washed three times with phosphate-buffered saline (PBS) containing Triton X-100 (0.02 phosphate, 150 mM NaCl, 0.1% Triton X-100).

The HA-tagged N48K Clarin-1 was detected with an antibody against the HA tag (HA.11 Clone 16B12 Monoclonal antibody, Covance #MMS-101P) at a dilution of 1:1000 in PBS containing Triton X-100. After a 90 min incubation, wells were washed three times with PBS containing Triton X-100, and a secondary antibody (Goat anti-mouse IgG-Cy3 (1.5 mg/ml), Jackson IR Europe #115165003) was added to the wells at a dilution of 1:250 in PBS containing Triton X-100 for 45 min. Wells were subsequently washed three times with PBS containing Triton X-100, and a final staining for nuclei was performed by the addition of DAPI (4',6-diamidino-2-phenylindole) at a dilution of 1:10,000. The imaging of the stained cells was performed on an InCell 1000 High Content Imager (GE Healthcare), reading out the Cy3 channel for N48K Clarin-1 and the DAPI channel for nuclei. The images are analyzed and quantitated using a specific algorithm. This algorithm measured the HA-Clarin-1 staining for each cell based on the additional nuclear segmentation of the DAPI signal (FIG. 1). This algorithm measured the intensity per cell, and thus it is less sensitive for variation in cell number. Per well, approximately 2,000 cells were measured to achieve an average density per cell measurement.

Example 22

$IC_{50}$ Data for Illustrative Compounds of the Invention $IC_{50}$ values for Compounds 5-12 of the invention were obtained according to the assay method of Example 20. $IC_{50}$ values obtained for Compounds 5-12 were less than or equal to 2 micromolar.

$IC_{50}$ values for Compounds 1-4, 11, 13, and 14 were obtained according to the assay method of Example 21. The $IC_{50}$ values obtained for Compounds 1-4, 11, 13, and 14, were less than or equal to 14 micromolar. $IC_{50}$ values obtained for compounds 1-3, 11, 13, and 14, were less than or equal to 6 micromolar. $IC_{50}$ values obtained for compounds 2, 11, and 13 were less than or equal to 4 micromolar. The $IC_{50}$ value obtained for compound 13 was less than or equal to 1 micromolar.

The $IC_{50}$ value obtained for Compound 11 assayed according to the method of Example 20 was less than 2 micromolar. The $IC_{50}$ value obtained for Compound 11 assayed according to the method of Example 21 was less than 3 micromolar.

Each reference disclosed in this application is incorporated by reference herein in its entirety.

What is claimed is:

1. A compound having the structure:

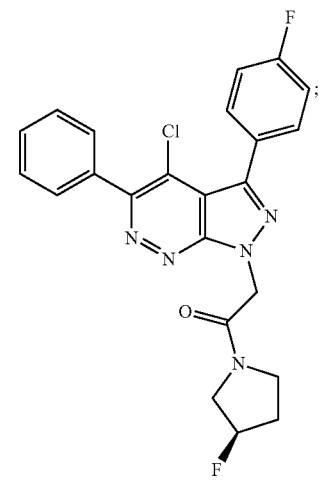

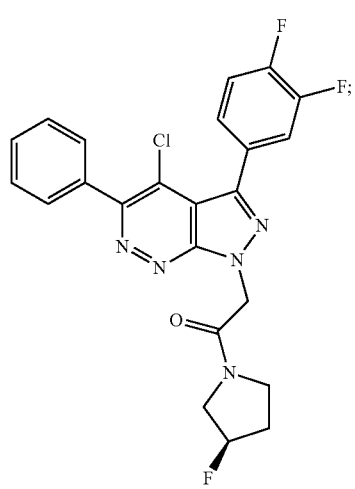

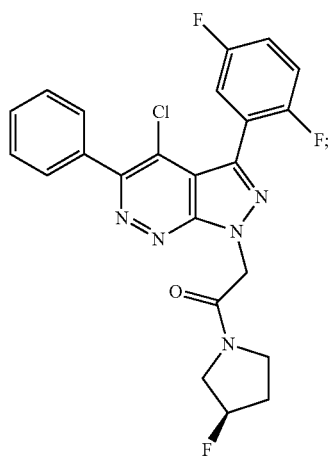

4
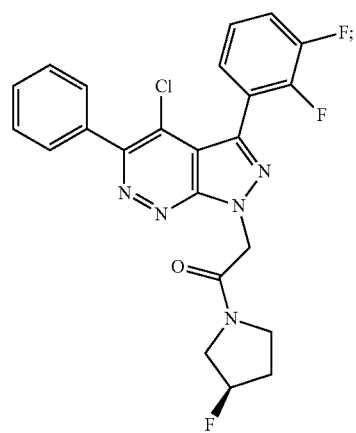
5
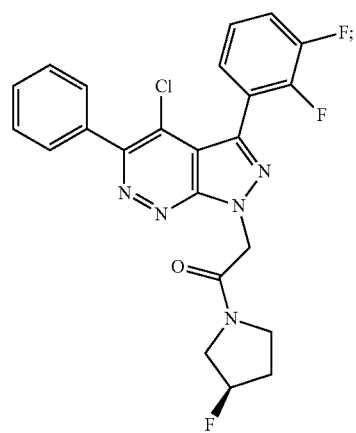
6
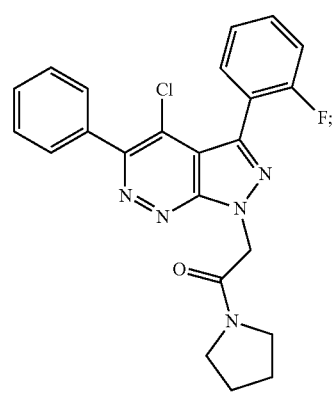
7
8
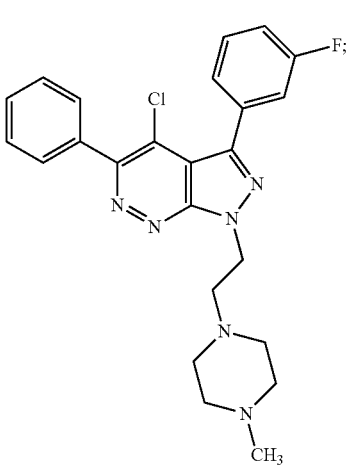
9
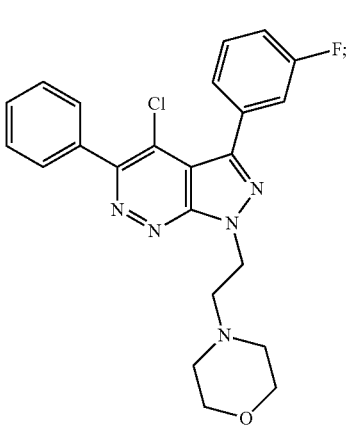
10
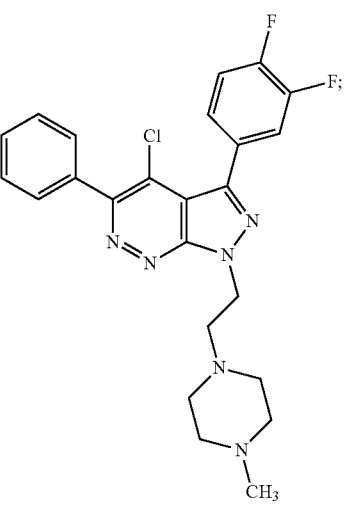

-continued

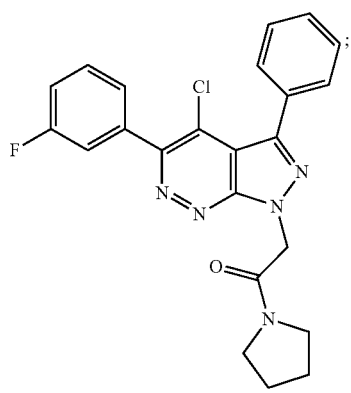
11

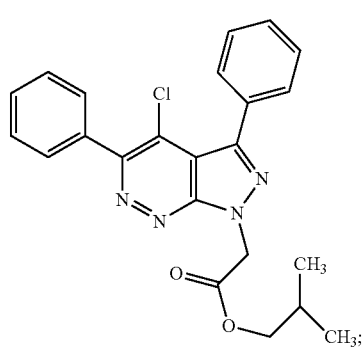
12

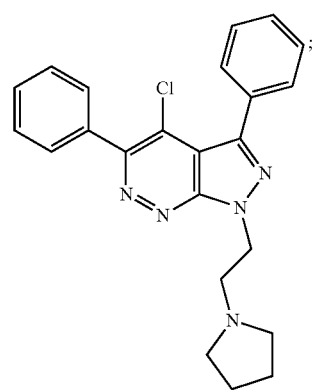
13 or a pharmaceutically acceptable salt thereof.

2. A composition comprising an effective amount of a compound or pharmaceutically acceptable salt of the compound of claim 1 and a pharmaceutically acceptable carrier or vehicle.

3. A method for treating a retinal degenerative disease, comprising administering to a subject in need thereof an effective amount of a compound or pharmaceutically acceptable salt of the compound of claim 1.

4. The method of claim 3, wherein the retinal degenerative disease is retinitis pigmentosa, Leber's congenital Amaurosis, Syndromic retinal degenerations, age-related macular degeneration, or Usher Syndrome.

5. The method of claim 4, wherein the Usher Syndrome is Usher I, Usher II or Usher III Syndrome.

6. The method of claim 3, wherein the retinal degenerative disease is Usher III Syndrome.

7. A method for treating hearing loss associated with Usher syndrome, comprising administering to a subject in need thereof an effective amount of a compound or pharmaceutically acceptable salt of the compound of claim 1.

8. The method of claim 7, wherein the Usher Syndrome is Usher I, Usher II or Usher III Syndrome.

9. The method of claim 7, wherein the Usher Syndrome is Usher III Syndrome.

10. A compound having the structure:

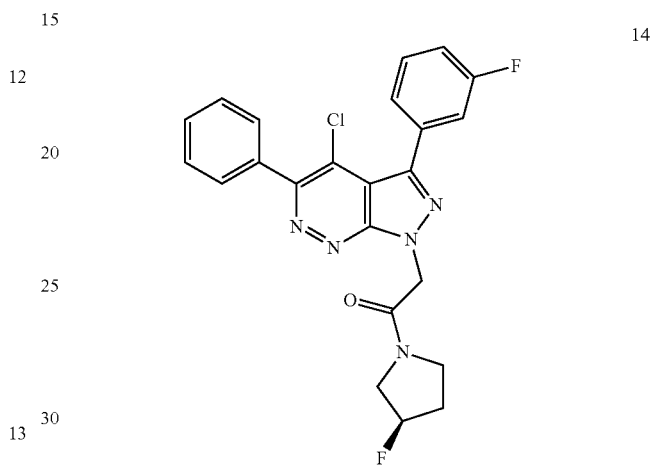
14 or a pharmaceutically acceptable salt thereof.

11. A composition comprising an effective amount of a compound or pharmaceutically acceptable salt of the compound of claim 10 and a pharmaceutically acceptable carrier or vehicle.

12. A method for treating a retinal degenerative disease, comprising administering to a subject in need thereof an effective amount of a compound or pharmaceutically acceptable salt of the compound of claim 10.

13. The method of claim 12, wherein the retinal degenerative disease is retinitis pigmentosa, Leber's congenital Amaurosis, Syndromic retinal degenerations, age-related macular degeneration, or Usher Syndrome.

14. The method of claim 13, wherein the Usher Syndrome is Usher I, Usher II or Usher III Syndrome.

15. The method of claim 12, wherein the retinal degenerative disease is Usher III Syndrome.

16. A method for treating hearing loss associated with Usher syndrome, comprising administering to a subject in need thereof an effective amount of a compound or pharmaceutically acceptable salt of the compound of claim 10.

17. The method of claim 16, wherein the Usher Syndrome is Usher I, Usher II or Usher III Syndrome.

18. The method of claim 16, wherein the Usher Syndrome is Usher III Syndrome.

* * * * *